United States Patent
Dath et al.

(10) Patent No.: US 6,977,321 B1
(45) Date of Patent: *Dec. 20, 2005

(54) PRODUCTION OF PROPYLENE

(75) Inventors: Jean-Pierre Dath, Beloeil (BE); Luc Delorme, Waterloo (BE); Jacques-François Grootjans, Leefdaal (BE); Xavier Vanhaeren, Genval (BE); Walter Vermeiren, Houthalen (BE)

(73) Assignee: Fina Research S.A., Feluy (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/205,056

(22) Filed: Dec. 3, 1998

(30) Foreign Application Priority Data

Dec. 5, 1997 (EP) .................................. 97121389

(51) Int. Cl.[7] .......................... C07C 4/06; C10G 11/05
(52) U.S. Cl. ..................... 585/653; 585/648; 208/118; 208/120.01; 208/212
(58) Field of Search ................................ 585/648, 653, 585/666, 670; 208/118, 121, 120.01

(56) References Cited

U.S. PATENT DOCUMENTS

| | | | |
|---|---|---|---|
| 3,506,400 A * | 4/1970 | Eberly, Jr. et al. | 423/713 |
| 3,702,886 A * | 11/1972 | Argauer et al. | 423/328 |
| 3,709,979 A * | 1/1973 | Chu | 423/328 |
| 5,026,936 A * | 6/1991 | Leyshon et al. | 585/315 |
| 5,599,956 A * | 2/1997 | Pujado et al. | 549/531 |
| 5,997,728 A * | 12/1999 | Adewuyi et al. | 208/120.01 |
| 6,171,556 B1 * | 1/2001 | Burk et al. | 422/173 |

FOREIGN PATENT DOCUMENTS

| | | | |
|---|---|---|---|
| EP | 0109059 | * | 5/1984 |
| EP | 0109060 | * | 5/1984 |
| GB | 1323710 | * | 7/1973 |

* cited by examiner

Primary Examiner—Walter D. Griffin
(74) Attorney, Agent, or Firm—William D. Jackson

(57) ABSTRACT

A process for the production of propylene from an olefinic feedstock containing at least one olefin of $C_4$ or greater, the process comprising contacting the olefinic feedstock with a catalyst of the MFI-type having a silicon/aluminum atomic ratio of at least about 180 to produce an effluent containing propylene, the propylene yield on an olefin basis being from 30 to 50k based on the olefinic content of the feedstock.

8 Claims, 9 Drawing Sheets

PRODUCTION OF PROPYLENE

BACKGROUND TO THE INVENTION

The present invention relates to a process for the production of propylene from an olefinic feedstock.

DESCRIPTION OF THE PRIOR ART

It is known in the art to use zeolites to convert long chain paraffins into lighter products, for example in the catalytic dewaxing of petroleum feedstocks. While it is not the objective of dewaxing, at least parts of the paraffinic hydrocarbons are converted into olefins. It is known in such processes to use crystalline silicates for example of the MFI type, the three-letter designation "MFI" representing a particular crystalline silicate structure type as established by the Structure Commission of the International Zeolite Association. Examples of a crystalline silicate of the MFI type are the synthetic zeolite ZSM-5 and silicalite and other MFI type crystalline silicates are known in the art.

GB-A-1323710 discloses a dewaxing process for the removal of straight-chain paraffins and slightly branched-chain paraffins, from hydrocarbon feedstocks utilising a crystalline silicate catalyst, in particular ZSM-5. U.S. Pat. No. 4,247,388 also discloses a method of catalytic hydrodewaxing of petroleum and synthetic hydrocarbon feedstocks using a crystalline silicate of the ZSM-5 type. Similar dewaxing processes are disclosed in U.S. Pat. No. 4,284,529 and U.S. Pat. No. 5,614,079. The catalysts are crystalline alumino-silicates and the above-identified prior art documents disclose the use of a wide range of Si/Al ratios and differing reaction conditions for the disclosed dewaxing processes.

GB-A-2185753 discloses the dewaxing of hydrocarbon feedstocks using a silicalite catalyst. U.S. Pat. No. 4,394,251 discloses hydrocarbon conversion with a crystalline silicate particle having an aluminum-containing outer shell.

It is also known in the art to effect selective conversion of hydrocarbon feeds containing straight-chain and/or slightly branched-chain hydrocarbons, in particular paraffins, into a lower molecular weight product mixture containing a significant amount of olefins. The conversion is effected by contacting the feed with a crystalline silicate known as silicalite, as disclosed in GB-A-2075045, U.S. Pat. No. 4,401,555 and U.S. Pat. No. 4,309,276. Silicalite is disclosed in U.S. Pat. No. 4,061,724.

Silicalite catalysts exist having varying silicon/aluminum atomic ratios and different crystalline forms. EP-A-0146524 and 0146525 in the name of Cosden Technology, Inc. disclose crystalline silicas of the silicalite type having monoclinic symmetry and a process for their preparation. These silicates have a silicon to aluminum atomic ratio of greater than 80.

WO-A-97/04871 discloses the treatment of a medium pore zeolite with steam followed by treatment with an acidic solution for improving the butene selectivity of the zeolite in catalytic cracking.

A paper entitled "De-alumination of HZSM-5 zeolites: Effect of steaming on acidity and aromatization activity", de Lucas et al, Applied Catalysis A: General 154 1997 221–240, published by Elsevier Science B. V. discloses the conversion of acetone/n-butanol mixtures to hydrocarbons over such dealuminated zeolites.

It is yet further known, for example from U.S. Pat. No. 4,171,257, to dewax petroleum distillates using a crystalline silicate catalyst such as ZSM-5 to produce a light olefin fraction, for example a $C_3$ to $C_4$ olefin fraction. Typically, the reactor temperature reaches around 500° C. and the reactor employs a low hydrocarbon partial pressure which favours the conversion of the petroleum distillates into propylene. Dewaxing cracks paraffinic chains leading to a decrease in the viscosity of the feedstock distillates, but also yields a minor production of olefins from the cracked paraffins.

EP-A-0305720 discloses the production of gaseous olefins by catalytic conversion of hydrocarbons. EP-B-0347003 discloses a process for the conversion of a hydrocarbonaceous feedstock into light olefins. WO-A-90/11338 discloses a process for the conversion of $C_2$–$C_{12}$ paraffinic hydrocarbons to petrochemical feedstocks, in particular to $C_2$ to $C_4$ olefins. U.S. Pat. No. 5,043,522 and EP-A-0395345 disclose the production of olefins from paraffins having four or more carbon atoms. EP-A-0511013 discloses the production of olefins from hydrocarbons using a steam activated catalyst containing phosphorous and H-ZSM-5. U.S. Pat. No. 4,810,356 discloses a process for the treatment of gas oils by dewaxing over a silicalite catalyst. GB-A-2156845 discloses the production of isobutylene from propylene or a mixture of hydrocarbons containing propylene. GB-A-2159833 discloses the production of a isobutylene by the catalytic cracking of light distillates.

It is known in the art that for the crystalline silicates exemplified above, long chain olefins tend to crack at a much higher rate than the corresponding long chain paraffins.

It is further known that when crystalline silicates are employed as catalysts for the conversion of paraffins into olefins, such conversion is not stable against time. The conversion rate decreases as the time on stream increases, which is due to formation of coke (carbon) which is deposited on the catalyst.

These known processes are employed to crack heavy paraffinic molecules into lighter molecules. However, when it is desired to produce propylene, not only are the yields low but also the stability of the crystalline silicate catalyst is low. For example, in an FCC unit a typical propylene output is 3.5 wt %. The propylene output may be increased to up to about 7–8 wt % propylene from the FCC unit by introducing the known ZSM-5 catalyst into the FCC unit to "squeeze" out more propylene from the incoming hydrocarbon feedstock being cracked. Not only is this increase in yield quite small, but also the ZSM-5 catalyst has low stability in the FCC unit.

There is an increasing demand for propylene in particular for the manufacture of polypropylene.

The petrochemical industry is presently facing a major squeeze in propylene availability as a result of the growth in propylene derivatives, especially polypropylene. Traditional methods to increase propylene production are not entirely satisfactory. For example, additional naphtha steam cracking units which produce about twice as much ethylene as propylene are an expensive way to yield propylene since the feedstock is valuable and the capital investment is very high. Naphtha is in competition as a feedstock for steam crackers because it is a base for the production of gasoline in the refinery. Propane dehydrogenation gives a high yield of propylene but the feedstock (propane) is only cost effective during limited periods of the year, making the process expensive and limiting the production of propylene. Propylene is obtained from FCC units but at a relatively low yield and increasing the yield has proven to be expensive and limited. Yet another route known as metathesis or disproportionation enables the production of propylene from ethylene and butene. Often, combined with a steam cracker, this technology is expensive since it uses ethylene as a feedstock which is at least as valuable as propylene.

EP-A-0109059 discloses a process for converting olefins having 4 to 12 carbon atoms into propylene. The olefins are contacted with an alumino-silicate having a crystalline and zeolite structure (e.g. ZSM-5 or ZSM-11) and having a $SiO_2/Al_2O_3$ molar ratio equal to or lower than 300. The specification requires high space velocities of greater than 50 kg/h per kg of pure zeolite in order to achieve high propylene yield. The specification also states that generally the higher the space velocity the lower the $SiO_2/Al_2O_3$ molar ratio (called the Z ratio). This specification only exemplifies olefin conversion processes over short periods (e.g. a few hours) and does not address the problem of ensuring that the catalyst is stable over longer periods (e.g. at least 160 hours or a few days) which are required in commercial production. Moreover, the requirement for high space velocities is undesirable for commercial implementation of the olefin conversion process.

Thus there is a need for a high yield propylene production method which can readily be integrated into a refinery or petrochemical plant, taking advantage of feedstocks that are less valuable for the market place (having few alternatives on the market).

On the other hand, crystalline silicates of the MFI type are also well known catalysts for the oligomerisation of olefins. For example, EP-A-0031675 discloses the conversion of olefin-containing mixtures to gasoline over a catalyst such as ZSM-5. As will be apparent to a person skilled in the art, the operating conditions for the oligomerisation reaction differ significantly from those used for cracking. Typically, in the oligomerisation reactor the temperature does not exceed around 400° C. and a high pressure favours the oligomerisation reactions.

GB-A-2156844 discloses a process for the isomerisation of olefins over silicalite as a catalyst. U.S. Pat. No. 4,579,989 discloses the conversion of olefins to higher molecular weight hydrocarbons over a silicalite catalyst. U.S. Pat. No. 4,746,762 discloses the upgrading of light olefins to produce hydrocarbons rich in $C_5$+ liquids over a crystalline silicate catalyst. U.S. Pat. No. 5,004,852 discloses a two-stage process for conversion of olefins to high octane gasoline wherein in the first stage olefins are oligomerised to $C_5$+ olefins. U.S. Pat. No. 5,171,331 discloses a process for the production of gasoline comprising oligomerising a $C_2$–$C_6$ olefin containing feedstock over an intermediate pore size siliceous crystalline molecular sieve catalyst such as silicalite, halogen stabilised silicalite or a zeolite. U.S. Pat. No. 4,414,423 discloses a multistep process for preparing high-boiling hydrocarbons from normally gaseous hydrocarbons, the first step comprising feeding normally gaseous olefins over an intermediate pore size siliceous crystalline molecular sieve catalyst. U.S. Pat. No. 4,417,088 discloses the dimerising and trimerising of high carbon olefins over silicalite. U.S. Pat. No. 4,417,086 discloses an oligomerisation process for olefins over silicalite. GB-A-2106131 and GB-A-2106132 disclose the oligomerisation of olefins over catalysts such as zeolite or silicalite to produce high boiling hydrocarbons. GB-A-2106533 discloses the oligomerisation of gaseous olefins over zeolite or silicalite.

SUMMARY OF THE INVENTION

It is an object of the present invention to provide a process for using the less valuable olefins present in refinery and petrochemical plants as a feedstock for a process which, in contrast to the prior art processes referred to above, catalytically converts olefins into lighter olefins, and in particular propylene.

It is another object of the invention to provide a process for producing propylene having a high propylene yield and purity.

It is a further object of the present invention to provide such a process which can produce propylene-containing effluents which are very rich in propylene, and are within, at least, a chemical grade quality.

It is yet a further object of the present invention to provide a process for producing propylene having a stable propylene conversion and a stable product distribution over time.

It is yet a further object of the present invention to provide a process for converting olefinic feedstocks having a high yield on an olefin basis towards propylene, irrespective of the origin and composition of the olefinic feedstock.

The present invention provides a process for the production of propylene from an olefinic feedstock containing at least one olefin of $C_4$ or greater, the process comprising contacting the olefinic feedstock with a catalyst of the MFI-type having a silicon/aluminum atomic ratio of at least about 180 to produce an effluent containing propylene, the propylene yield on an olefin basis being from 30 to 50% based on the olefinic content of the feedstock.

The present invention can thus provide a process wherein olefin-rich hydrocarbon streams (products) from refinery and petrochemical plants are selectively cracked not only into light olefins, but particularly into propylene. In one preferred embodiment the olefin-rich feedstock may be passed over a crystalline silicate catalyst with a particular Si/Al atomic ratio of from 180 to 1000 obtained after a steaming/de-alumination treatment. Alternatively the olefin-rich feedstock may be passed over a commercially available catalyst of the ZSM-5 type which has been prepared by crystallisation using an organic template and has been unsubjected to any subsequent steaming or de-alumination process, the catalyst having a silicon/aluminum atomic ratio of from 300 to 1000. The feedstock may be passed over the catalyst at a temperature ranging between 500 to 600° C., an olefin partial pressure of from 0.1 to 2 bars and an LHSV of from 10 to 30h$^{-1}$ to yield at least 30 to 50' propylene based on the olefin content in the feedstock.

In this specification, the term "silicon/aluminum atomic ratio" is intended to mean the Si/Al atomic ratio of the overall material, which may be determined by chemical analysis. In particular, for crystalline silicate materials, the stated Si/Al ratios apply not just to the Si/Al framework of the crystalline silicate but rather to the whole material.

The silicon/aluminum atomic ratio is greater than about 180. Even at silicon/aluminum atomic ratios less than about 180, the yield of light olefins, in particular propylene, as a result of the catalytic cracking of the olefin-rich feedstock may be greater than in the prior art processes. The feedstock may be fed either undiluted or diluted with an inert gas such as nitrogen. In the latter case, the absolute pressure of the feedstock constitutes the partial pressure of the hydrocarbon feedstock in the inert gas.

BRIEF DESCRIPTION OF THE DRAWINGS

The various aspects of the present invention will now be described in greater detail however by example only with reference to the accompanying drawings, in which.

DETAILED DESCRIPTION OF THE PREFERRED EMBODIMENTS

Figure 1:
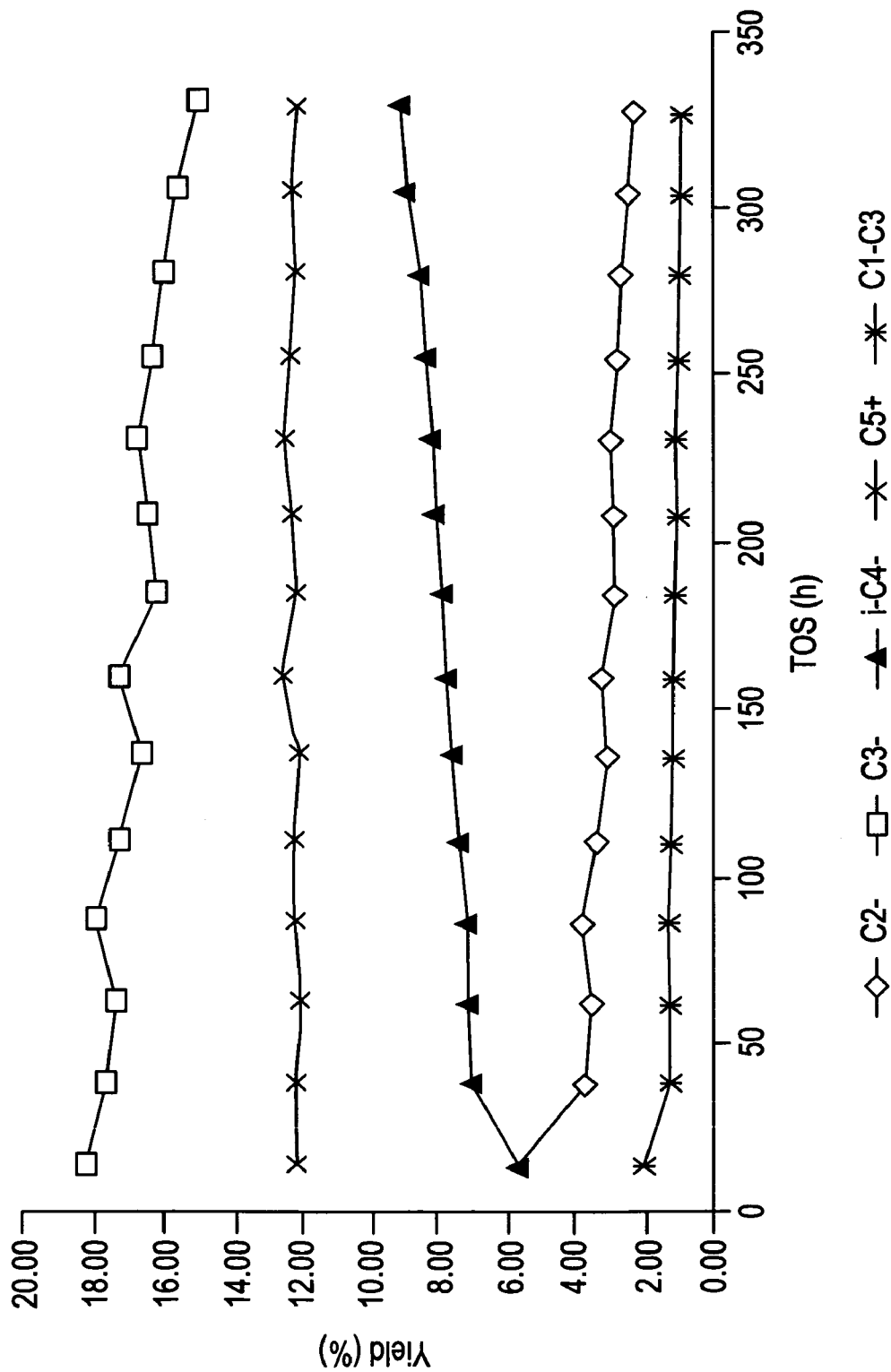
FIGS. 1 and 2 are graphs showing the relationship between the yield of various products, including propylene, and time for a catalytic cracking process in accordance with an Example of the invention and in accordance with a comparative Example respectively.

In accordance with the present invention, cracking of olefins is performed in the sense that olefins in a hydrocarbon stream are cracked into lighter olefins and selectively into propylene. The feedstock and effluent preferably have substantially the same olefin content by weight. Typically, the olefin content of the effluent is within ±15 wt %, more preferably ±10 wt %, of the olefin content of the feedstock. The feedstock may comprise any kind of olefin-containing hydrocarbon stream provided that it contains one or more olefins of $C_4$ or greater. The feedstock may typically comprise from 10 to 100 wt % olefins and furthermore may be fed undiluted or diluted by a diluent, the diluent optionally including a non-olefinic hydrocarbon. In particular, the olefin-containing feedstock may be a hydrocarbon mixture containing normal and branched olefins in the carbon range $C_4$ to $C_{10}$, more preferably in the carbon range $C_4$ to $C_6$, optionally in a mixture with normal and branched paraffins and/or aromatics in the carbon range $C_4$ to $C_{10}$. Typically, the olefin-containing stream has a boiling point of from around −15 to around 180° C.

In particularly preferred embodiments of the present invention, the hydrocarbon feedstocks comprise $C_4$ mixtures from refineries and steam cracking units. Such steam cracking units crack a wide variety of feedstocks, including ethane, propane, butane, naphtha, gas oil, fuel oil, etc. Most particularly, the hydrocarbon feedstock may comprises a $C_4$ cut from a fluidized-bed catalytic cracking (FCC) unit in a crude oil refinery which is employed for converting heavy oil into gasoline and lighter products. Typically, such a $C_4$ cut from an FCC unit comprises around 50 wt % olefin. Alternatively, the hydrocarbon feedstock may comprise a $C_4$ cut from a unit within a crude oil refinery for producing methyl tert-butyl ether (MTBE) which is prepared from methanol and isobutene. Again, such a $C_4$ cut from the MTBE unit typically comprises around 50 wt % olefin. These $C_4$ cuts are fractionated at the outlet of the respective FCC or MTBE unit. The hydrocarbon feedstock may yet further comprise a $C_4$ cut from a naphtha steam-cracking unit of a petrochemical plant in which naphtha, comprising $C_5$ to $C_5$ species having a boiling point range of from about 15 to 180° C., is steam cracked to produce, inter alia, a $C_4$ cut. Such a $C_4$ cut typically comprises, by weight, 40 to 50% 1,3-butadiene, around 25% isobutylene, around 15% butene (in the form of but-1-ene and/or but-2-ene) and around 10' n-butane and/or isobutane. The olefin-containing hydrocarbon feedstock may also comprise a $C_4$ cut from a steam cracking unit after butadiene extraction (raffinate 1), or after butadiene hydrogenation.

The feedstock may yet further alternatively comprise a hydrogenated butadiene-rich $C_4$ cut, typically containing greater than 50 wt % $C_4$ as an olefin. Alternatively, the hydrocarbon feedstock could comprise a pure olefin feedstock which has been produced in a petrochemical plant.

The olefin-containing feedstock may yet further alternatively comprise light cracked naphtha (LCN) (otherwise known as light catalytic cracked spirit (LCCS)) or a $C_5$ cut from a steam cracker or light cracked naphtha, the light cracked naphtha being fractionated from the effluent of the FCC unit, discussed hereinabove, in a crude oil refinery. Both such feedstocks contain olefins. The olefin-containing feedstock may yet further alternatively comprise a medium cracked naphtha from such an FCC unit or visbroken naphtha obtained from a visbreaking unit for treating the residue of a vacuum distillation unit in a crude oil refinery.

The olefin-containing feedstock may comprise a mixture of one or more of the above-described feedstocks.

The use of a $C_5$ cut as the olefin-containing hydrocarbon feedstock in accordance with a preferred process of the invention has particular advantages because of the need to remove $C_5$ species in any event from gasolines produced by the oil refinery. This is because the presence of $C_5$ in gasoline increases the ozone potential and thus the photochemical activity of the resulting gasoline. In the case of the use of light cracked naphtha as the olefin-containing feedstock, the olefin content of the remaining gasoline fraction is reduced, thereby reducing the vapour pressure and also the photochemical activity of the gasoline.

When converting light cracked naphtha, $C_2$ to $C_4$ olefins may be produced in accordance with the process of the invention. The $C_4$ fraction is very rich in olefins, especially in isobutene, which is an interesting feed for an MTBE unit. When converting a $C_4$ cut, $C_2$ to $C_3$ olefins are produced on the one hand and $C_5$ to $C_6$ olefins containing mainly iso-olefins are produced on the other hand. The remaining $C_4$ cut is enriched in butanes, especially in isobutane which is an interesting feedstock for an alkylation unit of an oil refinery wherein an alkylate for use in gasoline is produced from a mixture of $C_3$ and $C_5$ feedstocks. The $C_5$ to $C_6$ cut containing mainly iso-olefins is an interesting feed for the production of tertiary amyl methyl ether (TAME).

Surprisingly, the present inventors have found that in accordance with the process of the invention, olefinic feedstocks can be converted selectively so as to redistribute the olefinic content of the feedstock in the resultant effluent. The catalyst and process conditions are selected whereby the process has a particular yield on an olefin basis towards a propylene. Typically, the catalyst and process conditions are chosen whereby the process has the same high yield on an olefin basis towards propylene irrespective of the origin of the olefinic feedstocks for example the $C_4$ cut from the FCC unit, the $C_4$ cut from the MTBE unit, the light cracked naphtha or the $C_5$ cut from the light crack naphtha, etc., This is quite unexpected on the basis of the prior art. The propylene yield on an olefin basis is from 30 to 50% based on the olefin content of the feedstock. The yield on an olefin basis of a particular olefin is defined as the weight of that olefin in the effluent divided by the initial total olefin content by weight. For example, for a feedstock with 50 wt % olefin, if the effluent contains 20 wt % propylene, the propylene yield on an olefin basis is 40%. This may be contrasted with the actual yield for a product which is defined as the weight amount of the product produced divided by the weight amount of the feed. The paraffins and the aromatics contained in the feedstock are only slightly converted in accordance with the preferred aspects of the invention.

In accordance with preferred aspects of the present invention, the catalyst for the cracking of the olefins comprises a crystalline silicate of the silicalite type or of the ZSM-5 type, these in turn being in the MFI family of crystalline silicates.

The preferred crystalline silicates have pores or channels defined by ten oxygen rings and a high silicon/aluminum atomic ratio.

Crystalline silicates are microporous crystalline inorganic polymers based on a framework of $XO_4$ tetrahedra linked to each other by sharing of oxygen ions, where X may be trivalent (e.g. Al, B, . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bidirectional intersecting pore system with the following pore diameters: a straight channel along [010]:0.53–0.56 nm and a sinusoidal channel along [100]:0.51–0.55 nm.

The crystalline silicate catalyst has structural and chemical properties and is employed under particular reaction conditions whereby the catalytic cracking readily proceeds. Different reaction pathways can occur on the catalyst. Under the preferred process conditions, having an inlet temperature of around 500 to 600° C., more preferably from 520 to 600° C., yet more preferably 540 to 580° C., and an olefin partial pressure of from 0.1 to 2 bars, most preferably around atmospheric pressure, the shift of the double bond of an olefin in the feedstock is readily achieved, leading to double bond isomerisation. Furthermore, such isomerisation tends to reach a thermodynamic equilibrium. Propylene can be, for example, directly produced by the catalytic cracking of hexene or a heavier olefinic feedstock. Olefinic catalytic cracking may be understood to comprise a process yielding shorter molecules via bond breakage.

The catalyst has a high silicon/aluminum atomic ratio, i.e. at least about 180, preferably from about 180 to 1000, preferably greater than about 200, more preferably greater than about 300, whereby the catalyst may have relatively low acidity. Hydrogen transfer reactions are directly related to the strength and density of the acid sites on the catalyst, and such reactions are preferably suppressed so as to avoid the formation of coke during the olefin conversion process, which in turn would otherwise decrease the stability of the catalyst over time. Such hydrogen transfer reactions tend to produce saturates such as paraffins, intermediate unstable dienes and cyclo-olefins, and aromatics, none of which favours cracking into light olefins. Cyclo-olefins are precursors of aromatics and coke-like molecules, especially in the presence of solid acids, i.e. an acidic solid catalyst. The acidity of the catalyst can be determined by the amount of residual ammonia on the catalyst following contact of the catalyst with ammonia which adsorbs to the acid sites on the catalyst with subsequent ammonium desorption at elevated temperature measured by differential thermogravimetric analysis. Preferably, the silicon/aluminum ratio ranges from 180 to 1000, most preferably from 300 to 500.

One of the features of the invention is that with such high silicon/aluminum ratio in the crystalline silicate catalyst, a stable olefin conversion can be achieved with a high propylene yield on an olefin basis of from 30 to 50% whatever the origin and composition of the olefinic feedstock. Such high ratios reduce the acidity of the catalyst, thereby increasing the stability of the catalyst.

In accordance with one preferred aspect of the invention, the catalyst having a high silicon/aluminum atomic ratio for use in the catalytic cracking process of the present invention may be manufactured by removing aluminum from a commercially available silicalite. A typical commercially available silicalite has a silicon/aluminum atomic ratio of around 120. In accordance with the present invention, the commercially available silicalite may be modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the olefinic cracking processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the crystalline silicate. In this way by removing aluminum from the crystalline silicate framework and then removing alumina formed therefrom from the pores, the process aims at achieving a substantially homogeneous de-alumination throughout the whole pore surfaces of the catalyst. This reduces the acidity of the catalyst, and thereby reduces the occurrence of hydrogen transfer reactions in the cracking process. The reduction of acidity ideally occurs substantially homogeneously throughout the pores defined in the crystalline silicate framework. This is because in the olefin cracking process hydrocarbon species can enter deeply into the pores. Accordingly, the reduction of acidity and thus the reduction in hydrogen transfer reactions which would reduce the stability of the catalyst are pursued throughout the whole pore structure in the framework. In a preferred embodiment, the framework silicon/aluminum ratio is increased by this process to a value of at least about 180, preferably from about 180 to 1000, more preferably at least 200, yet more preferably at least 300, and most preferably around 480.

In accordance with an alternative preferred aspect of the invention the catalyst is a commercially available catalyst of the ZSM-5 type (for example a ZSM-5 type catalyst available in commerce from the company CU Chemie Ueticon AG of Switzerland under the trade name ZEOCAT P2-2) having a silicon/aluminum atomic ratio of at least 300, preferably from 300 to 1000.

The crystalline silicate, i.e. silicalite, catalyst is mixed with a binder, preferably an inorganic binder, and shaped to a desired shape, e.g. pellets. The binder is selected so as to be resistant to the temperature and other conditions employed in the catalyst manufacturing process and in the subsequent catalytic cracking process for the olefins. The binder is an inorganic material selected from clays, silica, metal oxides such as $ZrO_2$ and/or metals, or gels including mixtures of silica and metal oxides. The binder is preferably alumina-free. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica.

The relative proportions of the finely divided crystalline silicate material and the inorganic oxide matrix of the binder can vary widely. Typically, the binder content ranges from 5 to 95% by weight, more typically from 20 to 50' by weight, based on the weight of the composite catalyst. Such a mixture of crystalline silicate and an inorganic oxide binder is referred to as a formulated crystalline silicate.

In mixing the catalyst with a binder, the catalyst may be formulated into pellets, extruded into other shapes, or formed into a spray-dried powder.

Typically, the binder and the crystalline silicate catalyst are mixed together by an extrusion process. In such a process, the binder, for example silica, in the form of a gel is mixed with the crystalline silicate catalyst material and the resultant mixture is extruded into the desired shape, for example pellets. Thereafter, the formulated crystalline silicate is calcined in air or an inert gas, typically at a temperature of from 200 to 900° C. for a period of from 1 to 48 hours.

The binder preferably does not contain any aluminum compounds, such as alumina. This is because as mentioned above the preferred catalyst for use in the invention is de-aluminated to increase the silicon/aluminum ratio of the crystalline silicate. The presence of alumina in the binder yields other excess alumina if the binding step is performed prior to the aluminum extraction step. If the aluminum-containing binder is mixed with the crystalline silicate catalyst following aluminum extraction, this re-aluminates the catalyst. The presence of aluminum in the binder would tend to reduce the olefin selectivity of the catalyst, and to reduce the stability of the catalyst over time.

In addition, the mixing of the catalyst with the binder may be carried out either before or after the steaming and extraction steps.

The steam treatment is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam treatment is preferably carried out for a period of from 1 to 200 hours, more preferably from 20 hours to 100 hours. As stated above, the steam treatment tends to reduce the amount of tetrahedral aluminum in the crystalline silicate framework, by forming alumina.

Following the steam treatment, the extraction process is performed in order to de-aluminate the catalyst by leaching. The aluminum is preferably extracted from silicalite by a complexing agent which tends to form a soluble complex with alumina. The complexing agent is preferably in an aqueous solution thereof. The complexing agent may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The complexing agent for aluminum preferably forms a water-soluble complex with aluminum, and in particular removes alumina which is formed during the steam treatment step from the silicalite. A particularly preferred complexing agent may comprise an amine, preferably ethylene diamine tetraacetic acid (EDTA) or a salt thereof, in particular the sodium salt thereof.

Following the de-alumination step, the catalyst is thereafter calcined, for example at a temperature of from 400 to 800° C. at atmospheric pressure for a period of from 1 to 10 hours.

The various preferred catalysts of the present invention have been found to exhibit high stability, in particular being capable of giving a stable propylene yield over several days, e.g. up to ten days. This enables the olefin cracking process to be performed continuously in two parallel "swing" reactors wherein when one reactor is operating, the other reactor is undergoing catalyst regeneration. The catalyst of the present invention also can be regenerated several times. The catalyst is also flexible in that it can be employed to crack a variety of feedstocks, either pure or mixtures, coming from different sources in the oil refinery or petrochemical plant and having different compositions.

In the process for catalytic cracking of olefins in accordance with the invention, the present inventors have discovered that when dienes are present in the olefin-containing feedstock, this can provoke a faster deactivation of the catalyst. This can greatly decrease the yield on an olefin basis of the catalyst to produce the desired olefin, for example propylene, with increasing time on stream. The present inventors have discovered that when dienes are present in the feedstock which is catalytically cracked, this can yield a gum derived from the diene being formed on the catalyst which in turn decreases the catalyst activity. It is desired in accordance with the process of the invention for the catalyst to have a stable activity over time, typically for at least ten days.

In accordance with this aspect of the invention, prior to the catalytic cracking of the olefins, if the olefin-containing feedstock contains dienes, the feedstock is subjected to a selective hydrogenation process in order to remove the dienes. The hydrogenation process requires to be controlled in order to avoid the saturation of the mono-olefins. The hydrogenation process preferably comprises nickel-based or palladium-based catalysts or other catalysts which are typically used for first stage pyrolysis gasoline (Pygas) hydrogenation. When such nickel-based catalysts are used with a $C_4$ cut, a significant conversion of the mono-olefins into paraffins by hydrogenation cannot be avoided. Accordingly, such palladium-based catalysts, which are more selective to diene hydrogenation, are more suitable for use with the $C_4$ cut.

A particularly preferred catalyst is a palladium-based catalyst, supported on, for example, alumina and containing 0.2–0.8 wt % palladium based on the weight of the catalyst. The hydrogenation process is preferably carried out at an absolute pressure of from 5 to 50 bar, more preferably from 10 to 30 bar and at an inlet temperature of from 40 to 200° C. Typically, the hydrogen/diene weight ratio is at least 1, more preferably from 1 to 5, most preferably around 3. Preferably, the liquid hourly space velocity (LHSV) is at least $2h^{-1}$, more preferably from 2 to $5h^{-1}$.

The dienes in the feedstock are preferably removed so as to provide a maximum diene content in the feedstock of around 0.1% by weight, preferably around 0.05% by weight, more preferably around 0.03% by weight.

In the catalytic cracking process, the process conditions are selected in order to provide high selectivity towards propylene, a stable olefin conversion over time, and a stable olefinic product distribution in the effluent. Such objectives are favoured by the use of a low acid density in the catalyst (i.e. a high Si/Al atomic ratio) in conjunction with a low pressure, a high inlet temperature and a short contact time, all of which process parameters are interrelated and provide an overall cumulative effect (e.g. a higher pressure may be offset or compensated by a yet higher inlet temperature). The process conditions are selected to disfavour hydrogen transfer reactions leading to the formation of paraffins, aromatics and coke precursors. The process operating conditions thus employ a high space velocity, a low pressure and a high reaction temperature. Preferably, the LHSV ranges from 10 to $30h^{-1}$. The olefin partial pressure preferably ranges from 0.1 to 2 bars, more preferably from 0.5 to 1.5 bars. A particularly preferred olefin partial pressure is atmospheric pressure (i.e. 1 bar). The hydrocarbon feedstocks are preferably fed at a total inlet pressure sufficient to convey the feedstocks through the reactor. The hydrocarbon feedstocks may be fed undiluted or diluted in an inert gas, e.g. nitrogen. Preferably, the total absolute pressure in the reactor ranges from 0.5 to 10 bars. The present inventors have found that the use of a low olefin partial pressure, for example atmospheric pressure, tends to lower the incidence of hydrogen transfer reactions in the cracking process, which in turn reduces the potential for coke formation which tends to reduce catalyst stability. The cracking of the olefins is preferably performed at an inlet temperature of the feedstock of from 500 to 600° C., more preferably from 520 to 600° C., yet more preferably from 540 to 580° C., typically around 560° C. to 570° C.

The catalytic cracking process can be performed in a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" reactors.

Since the catalyst exhibits high stability to olefinic conversion for an extended period, typically at least around ten days, the frequency of regeneration of the catalyst is low. More particularly, the catalyst may accordingly have a lifetime which exceeds one year.

The olefin cracking process of the present invention is generally endothermic. Typically, propylene production from $C_4$ feedstocks tends to be less endothermic than from $C_5$ or light cracked naphtha feedstocks. For example for a light cracked naphtha having a propylene yield of around 18.4% (see Example 1), the enthalpy in was 429.9 kcal/kg and the enthalpy out was 346.9 kcal/kg. The corresponding values for a $C_5$-exLCN feedstock (see Example 2) were yield 16.8%, enthalpy in 437.9 kcal/kg and enthalpy out 358.3 kcal/kg and for a $C_4$-exMTBE feedstock (see Example 3) were yield 15.2%, enthalpy in 439.7/kg and enthalpy out 413.7 kcal/kg. Typically, the reactor is operated under adiabatic conditions and most typical conditions are an inlet temperature for the feedstock of around 570° C., an olefin partial pressure at atmospheric pressure and an LHSV for the feedstock of around $25h^{-1}$. Because the catalytic cracking process for the particular feedstock employed is endothermic, the temperature of the output effluent is correspondingly lowered. For example, for the liquid cracked naphtha, $C_5$-exLCN and the $C_4$-exMTBE feedstocks referred to above the typical adiabatic $\Delta T$ as a result of the endothermic process is 109.3, 98.5 and 31.1° C. respectively.

Thus for a $C_4$ olefinic stream, a temperature drop of around 30° C. would arise in an adiabatic reactor, whereas for LCN and $C_5$-exLCN streams, the temperature drop is significantly higher, namely around 109 and 98° C. respectively. If two such feedstocks are combined and fed jointly to the reactor, this can lead to a decrease in the overall heat duty of the selective cracking process. Accordingly, a blending of a $C_4$ cut with a $C_5$ cut or light cracked naphtha can reduce the overall heat duty of the process. Thus if for example a $C_4$ cut from the MTBE unit were combined with a light cracked naphtha to produce a composite feedstock, this decreases the heat duty of the process and leads to less energy being required to make the same amount of propylene.

After the catalytic cracking process, the reactor effluent is sent to a fractionator and the desired olefins are separated from the effluent. When the catalytic cracking process is employed to produce propylene, the $C_3$ cut, containing at least 95% propylene, is fractionated and thereafter purified in order to remove all the contaminants such as sulphur species, arsine, etc. The heavier olefins of greater than $C_3$ can be recycled.

The present inventors have found that the use of a silicalite catalyst in accordance with the present invention which has been steamed and extracted, has particular resistance to reduction in the catalyst activity (i.e. poisoning) by sulphur-, nitrogen- and oxygen-containing compounds which are typically present in the feedstocks.

Industrial feedstocks can contain several kinds of impurities which could affect the catalysts used for cracking, for example methanol, mercaptans and nitrites in $C_4$ streams and mercaptans, thiophenes, nitrites and amines in light cracked naphtha.

Certain tests were performed to simulate feedstocks containing poisons wherein a feedstock of 1-hexene was doped with n-propylamine or propionitrile, each yielding 100 ppm by weight of N; 2-propyl mercaptan or thiophene, each yielding 100 ppm by weight of S; and methanol, yielding either 100 or 2000 ppm by weight of O. These dopants did not affect the catalyst performance, with respect to the activity of the catalyst over time.

In accordance with various aspects of the present invention, not only can a variety of different olefinic feedstocks be employed in the cracking process, but also, by appropriate selection of the process conditions and of the particular catalyst employed, the olefin conversion process can be controlled so as to produce selectively particular olefin distributions in the resultant effluents.

For example, in accordance with the invention, olefin-rich streams from refinery or petrochemical plants are cracked into propylene. The light fractions of the effluent, namely the $C_2$ and $C_3$ cuts, can contain more than 95% propylene. Such cuts are sufficiently pure to constitute chemical grade propylene feedstocks. The present inventors have found that the propylene yield on an olefin basis in such a process ranges from 30 to 50% based on the olefinic content of the feedstock which contains one or more olefins of $C_4$ or greater. In the process, the effluent has a different olefin distribution as compared to that of the feedstock, but substantially the same total olefin content.

The various aspects of the present invention are illustrated below with reference to the following non-limiting Examples.

EXAMPLE 1

In this example, a light cracked naphtha (LCN) was cracked over a crystalline silicate. The catalyst was silicalite, formulated with a binder, which had been subjected to a pre-treatment (as described hereinbelow) by being heated (in steam), subjected to a de-alumination treatment with a complex for aluminum thereby to extract aluminum therefrom, and finally calcined. Thereafter the catalyst was employed to crack olefins in a hydrocarbon feedstock with the effluent produced by the catalytic cracking process having substantially the same olefin content as in the feedstock.

In the pre-treatment of the catalyst, a silicalite available in commerce under the trade name S115 from the company UOP Molecular Sieve Plant of P.O. Box 11486, Linde Drive, Chickasaw, Ala. 36611, USA was extruded into pellets with a binder comprising precipitated silica, the binder comprising 50 wt % of the resultant silicalite/binder combination. In greater detail, 538 g of precipitated silica (available in commerce from Degussa AG of Frankfurt, Germany under the trade name FK500) was mixed with 1000 ml of distilled water. The resultant slurry was brought to a pH of 1 by nitric acid and mixed for a period of 30 minutes. Subsequently, 520 g of the silicalite S115, 15 g of glycerol and 45 g of tylose were added to the slurry. The slurry was evaporated until a paste was obtained. The paste was extruded to form 2.5 mm diameter cylindrical extrudates. The extrudates were dried at 110° C. for a period of 16 hours and then calcined at a temperature of 600° C. for a period of 10 hours. Thereafter the resultant silicalite catalyst formulated with the binder was subjected to steam at a temperature of 550° C. and at atmospheric pressure. The atmosphere comprised 72 vol % steam in nitrogen and the steaming was carried out for a period of 48 hours. Thereafter, 145.5 g of the steamed catalyst was treated with a complexing compound for aluminum comprising ethylene diamino tetra-acetate (EDTA) in solution (611 ml) as the sodium salt thereof and at a concentration of around 0.05M $Na_2EDTA$. The solution was refluxed for 16 hours. The slurry was then washed thoroughly with water. The catalyst was then ion exchanged with $NH_4Cl$ (480 ml of 0.1N for each 100 g of catalyst) under reflux conditions and finally washed, dried at 110° C. and calcined at 400° C. for 3 hours. The de-aluminating process increased the Si/Al ratio of the silicalite from an initial value of around 220 to a value of around 280.

The resultant silicalite had a monoclinic crystalline structure.

The catalyst was then crushed to a particle size of from 35–45 mesh.

The catalyst was then employed for cracking of a light cracked naphtha. 10 ml of the crushed catalyst were placed in a reactor tube and heated up to a temperature of from 560–570° C. A feed of light cracked naphtha was injected into the reactor tube at an inlet temperature of around 547° C., an outlet hydrocarbon pressure of 1 bar (i.e. atmospheric pressure) and at an LHSV rate of around $10h^{-1}$.

In Example 1 and the remaining Examples the outlet hydrocarbon pressure is specified. This comprises the sum of the olefin partial pressure and the partial pressure of any non-olefinic hydrocarbons in the effluent. For any given outlet hydrocarbon pressure, the olefin partial pressure can readily be calculated on the basis of the molar content of olefins in the effluent e.g. if the effluent hydrocarbons contain 50 mol % olefins, then the outlet olefin partial pressure is one half of the outlet hydrocarbon pressure.

The feed of light cracked naphtha had been subjected to a preliminary hydrogenation process in order to remove dienes therefrom. In the hydrogenation process, the light cracked naphtha and hydrogen were passed over a catalyst comprising 0.6 wt % palladium on an alumina support at an inlet temperature of around 130° C., an absolute pressure of around 30 bars and an LHSV of around $2h^{-1}$ in the presence of hydrogen, with the hydrogen/diene molar ratio being around 3.

Table 1 shows the composition in terms of $C_1$ to $C_8$ compounds of the initial LCN feed together with the subsequent hydrotreated feed following the diene hydrogenation process. The initial LCN had a distillation curve (measured by ASTM D 1160) defined as follows:

| distilled (vol %) | at |
|---|---|
| 1 vol % | 14.1° C. |
| 5 | 28.1 |
| 10 | 30.3 |
| 30 | 37.7 |
| 50 | 54.0 |
| 70 | 67.0 |
| 90 | 91.4 |
| 95 | 100.1 |
| 98 | 118.3 |

In Table 1, the letter P represents a paraffin species, the letter O represents an olefinic species, the letter D represents a diene species and the letter A represents an aromatic species. Table 1 also shows the composition of the effluent following the catalytic cracking process.

It may be seen from Table 1 that following the catalytic cracking process, the feedstock and the effluent had substantially the same olefin content therein. In other words, the LCN comprised around 45 wt % olefin and the effluent comprised around 46 wt % olefin. However, in accordance with the invention the composition of the olefins in the effluent was substantially altered by the catalytic cracking process and it may be seen that the amount of propylene in the effluent increased from an initial value of 0 to a value of 18.3805 wt % in the effluent. This provided a propylene yield on an olefin basis of 40.6% in the catalytic cracking process. This demonstrates that the process in accordance with the invention provides catalytic cracking of olefins to other olefins with, in this example, a high degree of propylene production.

The LCN comprised $C_4$ to $C_8$ hydrocarbons and in the effluent, more than 40, for example around 51%, of the olefin content was present as $C_2$ to $C_3$ olefins. This demonstrates that the catalytic cracking process of the present invention produces a high yield of lower olefins from a light cracked naphtha feedstock. The olefins of the effluent comprised around 39 wt % propylene.

The catalytic cracking process significantly increases the $C_2$ to $C_4$ olefins of the effluent relative to the LCN feedstock and accordingly the amount of $C_5+$ hydrocarbon species in the effluent is significantly decreased relative to the LCN feedstock. This is clearly shown in Table 2 where it may be seen that the amount of $C_5+$ species in the effluent is significantly decreased to a value of around 63 wt % as compared to an initial value of around 96 wt % in the LCN feedstock. Table 2 also shows the composition of $C_5+$ species in the initial LCN feedstock; the hydrotreated LCN feedstock and in the effluent. The increase in $C_2$ to $C_4$ species in the effluent results in those species being readily fractionatable, as lighter olefins, from the effluent. This in turn yields a $C_5+$ liquid product having a composition shown in Table 2 with a significantly reduced olefin content in the LCN as compared to the initial LCN feedstock. This is a result of the $C_5+$ olefins in the initial LCN feedstock having been converted into $C_2$ to $C_4$ lighter olefins.

Referring to Table 3, this shows the hydrocarbon number of the $C_2$ to $C_4$ species in the initial LCN feedstock, the hydrotreated LCN feedstock and in the effluent. It may be seen from the $C_3$ species in the effluent, there being no $C_3$ species in the LCN feed, that practically all the $C_3$ is present as propylene. Thus if the $C_3$ species are fractionated from the effluent, the propylene purity is sufficiently high for the $C_3$ fraction that it can be used as a polymer starting material for the manufacture of polypropylene.

EXAMPLE 2

Example 1 was repeated but using a different feedstock comprising, rather than a light cracked naphtha, a fractionated $C_5$ cut from a light cracked naphtha. In addition, in the catalytic cracking process the inlet temperature was 548° C. The hydrocarbon outlet pressure was around 1 bar (i.e. atmospheric pressure).

Table 4 shows the distribution of the hydrocarbon species in the feed of the $C_5$ cut from the LCN, in the hydrotreated feed which had been subjected to a diene hydrogenation process as in Example 1, and in the effluent after the cracking process. It may be seen that the feed substantially initially comprises $C_5$ species and that following the catalytic cracking process, the olefin content has remained substantially the same but the amount of $C_5$ species in the effluent is significantly decreased as compared to the amount of such species in the initial feedstock. Again, the $C_2$ to $C_4$ lighter olefins may readily be fractionated from the effluent, leaving a $C_5+$ liquid product having a composition shown in Table 5. Table 6 shows a composition of the $C_2$ to $C_4$ hydrocarbon species. Again, it may be seen that the catalytic cracking process has a high propylene yield on an olefin basis of around 34%. Around 49.5% of the olefins in the effluent are present as $C_2$ to $C_3$ olefins, and more than 35% of the olefins in the effluent are comprised of propylene. Moreover, more than 95 of the $C_2$ to $C_3$ compounds are present as $C_2$ to $C_3$ olefins.

The effluent has an olefin content wherein around 49.5% of the olefin content is present as $C_2$ to $C_3$ olefins. This example shows that $C_2$ to $C_3$ olefins can be produced from a $C_5$ olefinic feedstock.

EXAMPLE 3

Example 1 was repeated but using as the feedstock, instead of a light cracked naphtha, a $C_4$ raffinate (raffinate II) from an MTBE unit in a refinery. In addition, the inlet temperature of the feedstock was around 560° C. The hydrocarbon outlet pressure was around 1 bar (atmospheric pressure).

It may be seen from Tables 7 to 9 that $C_2$ and primarily $C_3$ olefins are produced from the $C_4$ olefinic feedstock in accordance with the invention. In the effluent, around 34.5% of the olefin content is present as $C_2$ and/or $C_3$ olefins. The $C_2$ and/or $C_3$ olefins may be readily be fractionated from the effluent. The propylene yield on an olefin basis was 29%.

EXAMPLE 4

This example illustrates the catalytic cracking of an olefin feedstock comprising 1-hexene over silicalite which has been subjected to a steaming and de-alumination process and calcination, with the catalytic cracking process being performed at a variety of inlet temperatures for the feed into the reactor tube.

The silicalite catalyst comprised a silicalite having a silicon/aluminum ratio of around 120, and having a crystallite size of from 4 to 6 microns and a surface area (BET) of 399 $m^2$/g. The silicalite was pressed, washed and the 35–45 mesh fraction was retained. The silicalite was subjected to a steaming process in an atmosphere of 72 vol % stream and 28 vol % nitrogen at a temperature of 550° C. at atmospheric pressure for a period of 48 hours. Then 11 g of the steamed silicalite was treated with an EDTA solution (100 ml containing 0.0225M of $Na_2$ EDTA) thereby to de-aluminate the silicalite under reflux for a period of 6 hours. The slurry was then washed thoroughly with water. The catalyst was then subjected to ion exchange under reflux with ammonium chloride (100 ml of 0.05 N per 10 g of catalyst), washed, dried at 110° C. and finally calcined at 400° C. for 3 hours in a manner similar to that described in Example 1. The catalyst had a silicon/aluminum atomic ratio following the de-alumination treatment of around 180.

The silicalite was in its monoclinic crystalline form.

The crushed catalyst was then placed in a reactor tube and heated up to a temperature of around 580° C. The 1-hexene feed was injected at various inlet temperatures as specified in Table 10, at an outlet hydrocarbon pressure of 1 bar (atmospheric pressure) and at an LHSV of around $25h^{-1}$. Table 10 shows the composition of the $C_1$ to $C_6+$ species of the effluent produced in the various Runs 1–5 having inlet temperatures varying from around 507 to 580° C. The yield stated in Table 10 represents, since the feed comprises 100% olefin, both the propylene yield on an olefin basis and the actual yield of propylene defined as the weight amount of propylene/weight amount of feed×100%.

It may be seen that the propylene yield on an olefin basis increases with increasing inlet temperature and varies from around 28 at a temperature of around 507° C. to a value of around 47 at an inlet temperature of around 580° C.

It may be seen that the effluent contained a number of olefins having a lighter olefin content than the originating 1-hexene feedstock.

EXAMPLE 5

In this Example the feedstock comprised a $C_4$ stream comprising a raffinate II stream from an MTBE unit in a refinery. The $C_4$ feed had an initial composition as specified in Table 11.

In the catalytic cracking process, the catalyst comprised a silicalite catalyst prepared in accordance with the conditions described in Example 4.

The silicalite catalyst thus had a monoclinic crystalline structure and a silicon/aluminum atomic ratio of around 180.

The catalyst was placed in a reactor tube and heated up to a temperature of around 550° C. Thereafter the $C_4$ raffinate II feed was injected into the reactor tube at a rate having an LHSV feed of around $30h^{-1}$ and at the variable inlet temperatures and outlet hydrocarbon pressures as specified for Runs 1 and 2 in Table 11. For Run 1 the outlet hydrocarbon pressure was 1.2 bara and for Run 2 the outlet hydrocarbon pressure was 3 bara. The composition of the resultant effluents is shown in Table 11. This shows the effect of pressure on propylene yield and paraffin formation (i.e. loss of olefins).

It may be seen that from both Runs 1 and 2, the effluent contained significant amounts of propylene, the amount of propylene and the propylene yield on an olefin basis being higher in Run 1 which was performed at an outlet hydrocarbon pressure of 1.2 bar as opposed to Run 2 which was performed at an outlet hydrocarbon pressure of 3 bar.

In Run 1 the propylene yield on an olefin basis was 34.6% and in Run 2 the propylene yield on an olefin basis was 23.5%.

It may be seen that the cracking process in Run 1 produced $C_3$ olefins from primarily a $C_4$ olefinic feedstock. It may be seen that at least around 95% of the $C_3$ compounds are present as $C_3$ olefins in Run 1.

In Run 2, at higher pressure, more paraffins (propane, P5's) and heavy compounds ($C_6$+) were produced than in Run 1.

EXAMPLE 6

In this Example, a crystalline silicate, in particular a silicalite, catalyst having a high silicon/aluminum atomic ratio was produced, with silicalite powder being formulated with a binder.

The binder comprised silica. For forming the binder, 538 g of precipitated silica, available in commerce from Degussa AG, of GBAC, D-6000, Frankfurt, Germany, under the trade name FK500, was mixed with 1000 ml of distilled water. The resultant slurry was reduced to a pH of 1 with nitric acid and mixed for a period of around 30 minutes. Thereafter, the silicalite catalyst and the silica binder were combined by adding to the slurry 520 g of silicalite, available in commerce from the company UOP Molecular Sieve Plant of P.O. Box 11486, Linde Drive, Chickasaw, Ala. 36611, USA, under the trade name S115, together with 15 g of glycerol and 45 g of tylose. The slurry was evaporated until a paste was obtained. The paste was extruded to form 2.5 mm diameter cylindrical extrudates. The extrudates were dried at a temperature of around 110° C. for a period of around 16 hours. Thereafter, the dried pellets were calcined at a temperature of around 600° C. for a period of around 10 hours. The binder comprised 50 wt % of the composite catalyst.

The silicalite formulated with silica as binder were then subjected to a step of heating the catalyst in steam and thereafter extracting aluminum from the catalyst thereby to increase the Si/Al atomic ratio of the catalyst. The initial silicalite catalyst had a Si/Al atomic ratio of 220. The silicalite formulated with the silica binder in the extruded form was treated at a temperature of around 550° C. in a steam atmosphere comprising 72 vol % of steam and 28 vol % of nitrogen at atmospheric pressure for a period of 48 hours. The water partial pressure was 72 kPa. Thereafter, 145.5 g of the steamed catalyst was immersed in 611 ml of an aqueous solution comprising 0.05 M of $Na_2EDTA$ and the solution was refluxed for a period of 16 hours. The resultant slurry was then washed thoroughly with water. The catalyst was then ion-exchanged with ammonium chloride in an amount of 480 ml of 0.1N $NH_4Cl$ per 100 g of catalyst under reflux conditions. Finally, the catalyst was washed, dried at a temperature of around 110° C. and calcined at a temperature of around 400° C. for a period of around 3 hours.

The resultant catalyst had an Si/Al atomic ratio of higher than 280 and a monoclinic crystalline structure.

EXAMPLE 7

In this Example, a crystalline silicate catalyst having a high silicon/aluminum atomic ratio and based on silicalite was produced using a different order of steps from the process described in Example 6. In Example 7 the silicalite was formulated with a binder after steaming and de-alumination of the catalyst.

In an initial steam treatment step, silicalite available in commerce from the company UOP Molecular Sieve Plant of P.O. Box 11486, Linde Drive, Chickasaw, Ala. 36611, USA, under the trade name S115 and having an Si/Al atomic ratio of 220 was treated at a temperature of around 550° C. with steam in an atmosphere comprising 72 vol % of steam and 28 vol % of nitrogen at atmospheric pressure for a period of 48 hours. The water partial pressure was 72 kPa. Thereafter, 2 kg of the steamed catalyst was immersed in 8.4 liters of an aqueous solution containing 0.05 M of $Na_2EDTA$ and refluxed for a period of around 16 hours. The resultant slurry was washed thoroughly with water. Subsequently, the catalyst was ion-exchanged with ammonium chloride (4.2 liters of 0.1N $NH_4Cl$ per 1 kg of catalyst) under reflux conditions. Finally, the catalyst was washed, dried at a temperature of around 110° C. and calcined at a temperature of around 400° C. for a period of around 3 hours.

The resultant silicalite catalyst had an Si/Al atomic ratio of around 280 and a monoclinic crystalline structure.

The silicalite was thereafter formulated with an inorganic binder of silica. The silica was in the form of precipitated silica available in commerce from the company Degussa AG of GBAC, D-6000, Frankfurt, Germany, under the trade name FK500. 215 g of that silica was mixed with 850 ml of distilled water and the slurry was reduced to a pH of 1 with nitric acid and mixed for a period of 1 hour. Subsequently, 850 g of the above-treated silicalite, 15 g of glycerol and 45 g of tylose were added to the slurry. The slurry was then evaporated until a paste was obtained. The paste was extruded to form 1.6 mm diameter cylindrical extrudates. The extrudates were dried at a temperature of around 110° C. for a period of around 16 hours and thereafter calcined at a temperature of around 600° C. for a period of around 10 hours.

The binder comprised 20 wt % of the composite catalyst.

EXAMPLE 8 AND COMPARATIVE EXAMPLES 1 & 2

In Example 8, a silicalite catalyst which had been subjected to a steaming and de-alumination process by extraction was employed in the catalytic cracking of a feedstock comprising butene. The catalyst was a steamed and de-aluminated silicalite catalyst prepared in accordance with Example 4 and had a silicon/aluminum atomic ratio of 180.

In the catalytic cracking process, the butene-containing feedstock had the composition as specified in Table 12a.

The catalytic cracking process was carried out at an inlet temperature of 545° C., an outlet hydrocarbon pressure of atmospheric pressure and at an LSHV of $30h^{-1}$.

Table 12a shows the breakdown of the propylene, isobutene and n-butene amounts present in the effluent. It may be seen that the propylene amount is relatively high. It may also be noted that the silicalite exhibited stability over time in the catalytic cracking process, with the propylene selectivity being the same after a time on stream (TOS) of 20 hours and 164 hours. Thus the use of a catalyst produced in accordance with the invention provides a stable olefin conversion over time and yields a low formation of paraffins, in particular propane.

In contrast, Comparative Examples 1 and 2 used substantially the same feedstock and cracking conditions but in Comparative Example 1 the catalyst comprised the same starting silicalite as in Example 4 which had not been subjected to any steaming and extraction process and in Comparative Example 2 the catalyst comprised the same starting silicalite as in Example 4 which had been subject to the same steaming process as in Example 4, but not an extraction process. The results are shown in Tables 12b and 12c respectively. In each of Comparative Examples 1 and 2 the absence of an extraction process to remove aluminum from the framework of the silicalite yielded in the catalyst a significantly lower silicon/aluminum atomic ratio than for the catalyst of Example 8.

It may be seen that for Comparative Example 1 and Comparative Example 2 the catalyst did not exhibit stability. In other words, the catalyst reduced its ability over time to catalyse the cracking process. It is believed that this is because of the formation of coke on the catalyst, which in turn results from the use of a low silicon/aluminum atomic ratio in the catalyst, leading to a relatively high acidity for the catalyst.

For Comparative Example 1, there was also a significant formation of paraffins, e.g. propane.

EXAMPLES 9 AND 10

Examples 9 and 10 illustrate that by providing a high silicon/aluminum atomic ratio in a silicalite catalyst for use in a catalytic cracking process for olefins, this improves the stability of the catalyst.

FIG. 1 illustrates the variation between yield and time for a silicalite catalyst similar to that employed in Example 1 which had an initial silicon/aluminum atomic ratio of around 220 but had that ratio increased by the use of the steaming and de-alumination steps described in Example 1. It may be seen that the yield of propylene does not significantly decrease over time. This illustrates a high stability for the catalyst. The feedstock comprised a $C_4$ feedstock depleted in dienes.

Figure 2:
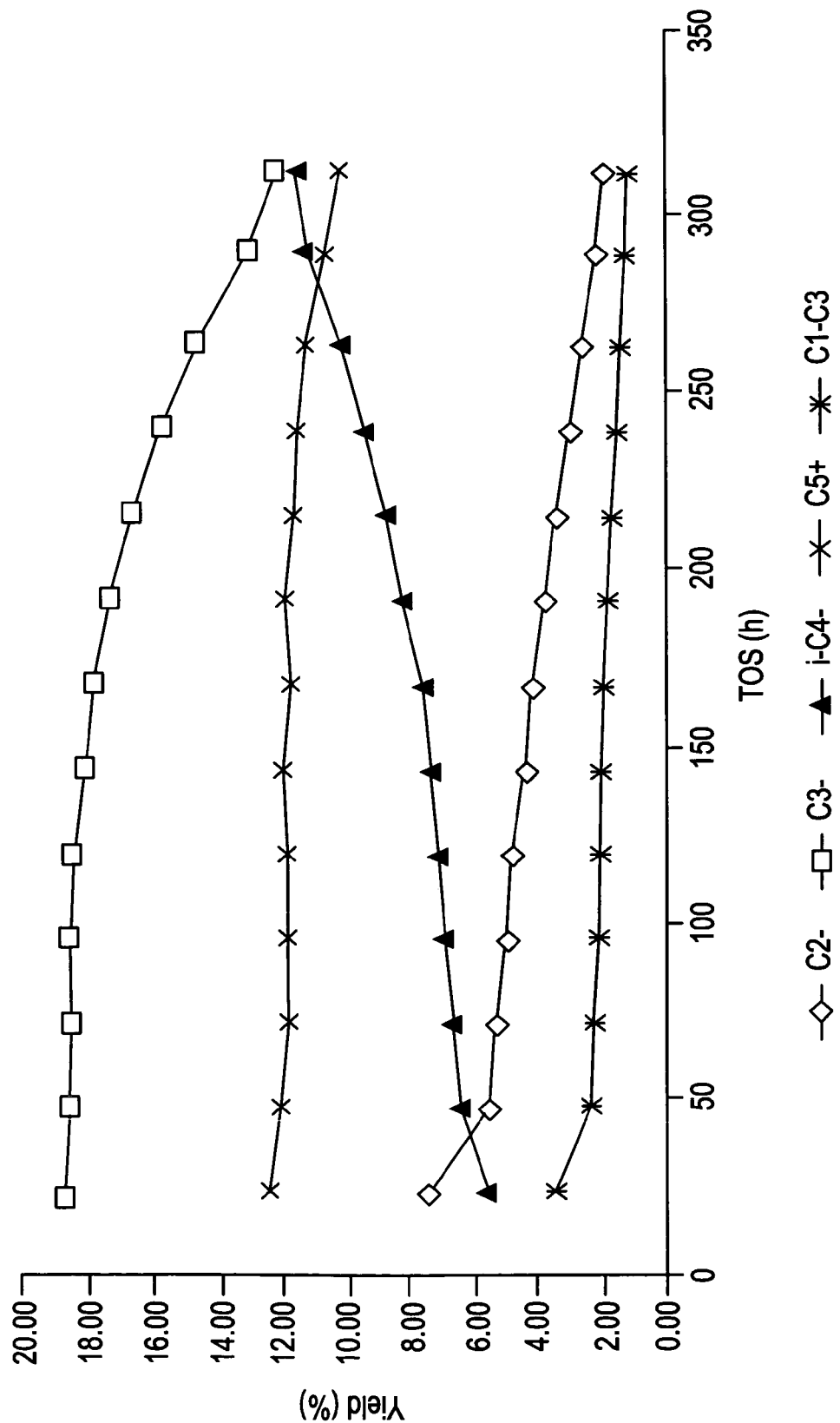

FIG. 2 shows for Example 10 how a silicalite catalyst having a lower silicon/aluminum atomic ratio leads to a reduction in the stability of the catalyst which is manifested in a decrease in the yield of propylene in a catalytic cracking process over time. In Example 10, the catalyst comprised the starting catalyst of Example 9 having a silicon/aluminum atomic ratio in the silicalite of around 220.

EXAMPLES 11–13 AND COMPARATIVE EXAMPLE 3

Figure 3:
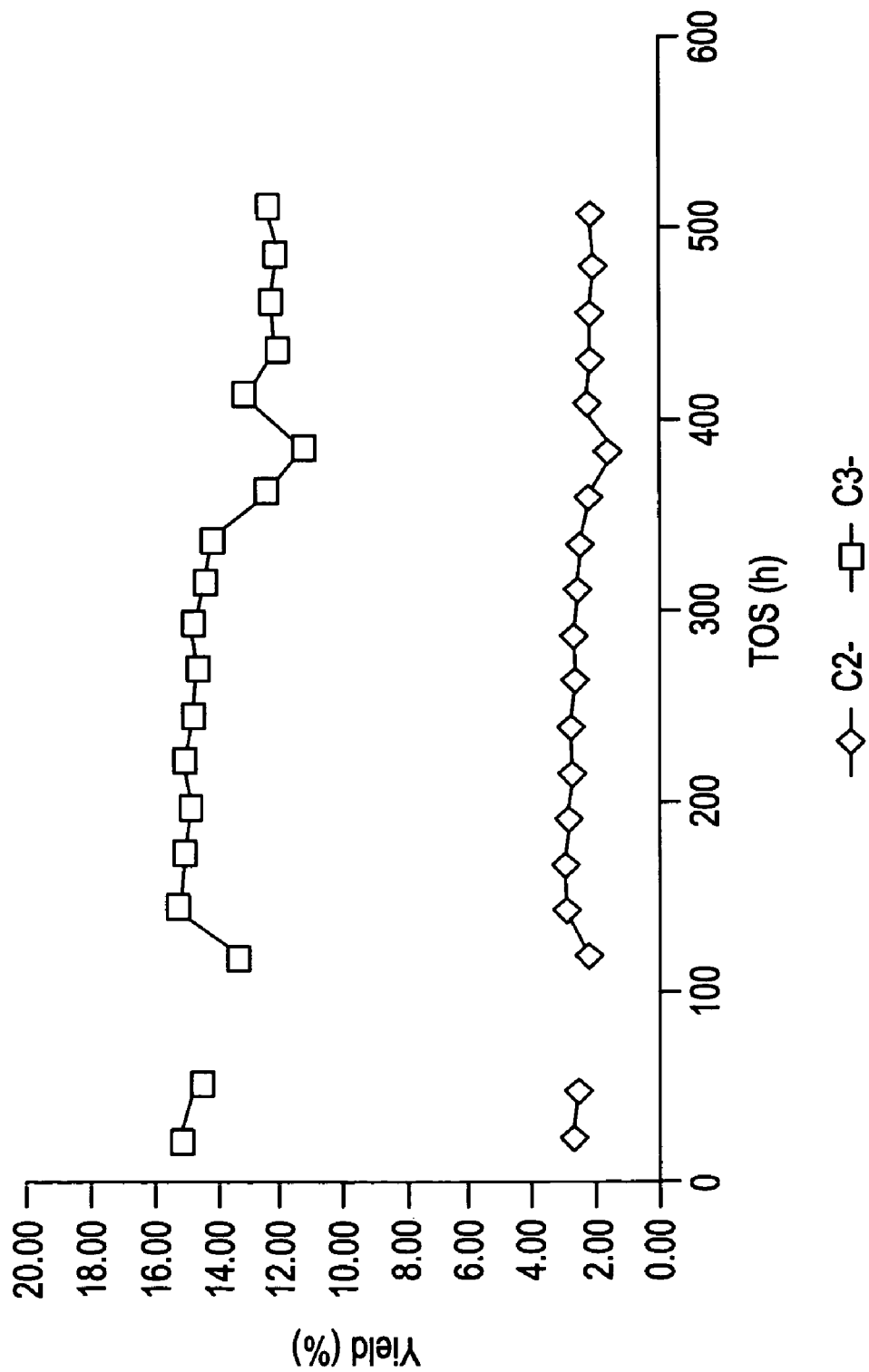
FIGS. 3 to 6 show the relationship between yield of, inter alia, propylene with time for catalysts having been manufactured using differing processing steps and differing binders.

In Examples 11 to 13, for Example 11 the variation of the yield of propylene with time was examined in a catalytic cracking process for an olefinic feedstock comprising $C_4$ depleted in dienes. The catalyst comprised the silicalite catalyst of Example 6, i.e. having an initial silicon/aluminum atomic ratio of 220 which had been subjected to an extrusion step with a binder comprising silica yielding a 50 wt % silica content in the extruded catalyst/binder composite. Such an extrusion process was similar to that disclosed with reference to Example 6. Thereafter the silicalite formulated with the binder was subjected to a steaming and extraction process as disclosed in Example 6. FIG. 3 illustrates the variation in the propylene yield over time in the catalytic cracking process. It may be seen that the propylene yield decreases only slightly even over a time on stream (TOS) of up to 500 hours which is substantially higher than a few hours or 169 hours.

Figure 4:
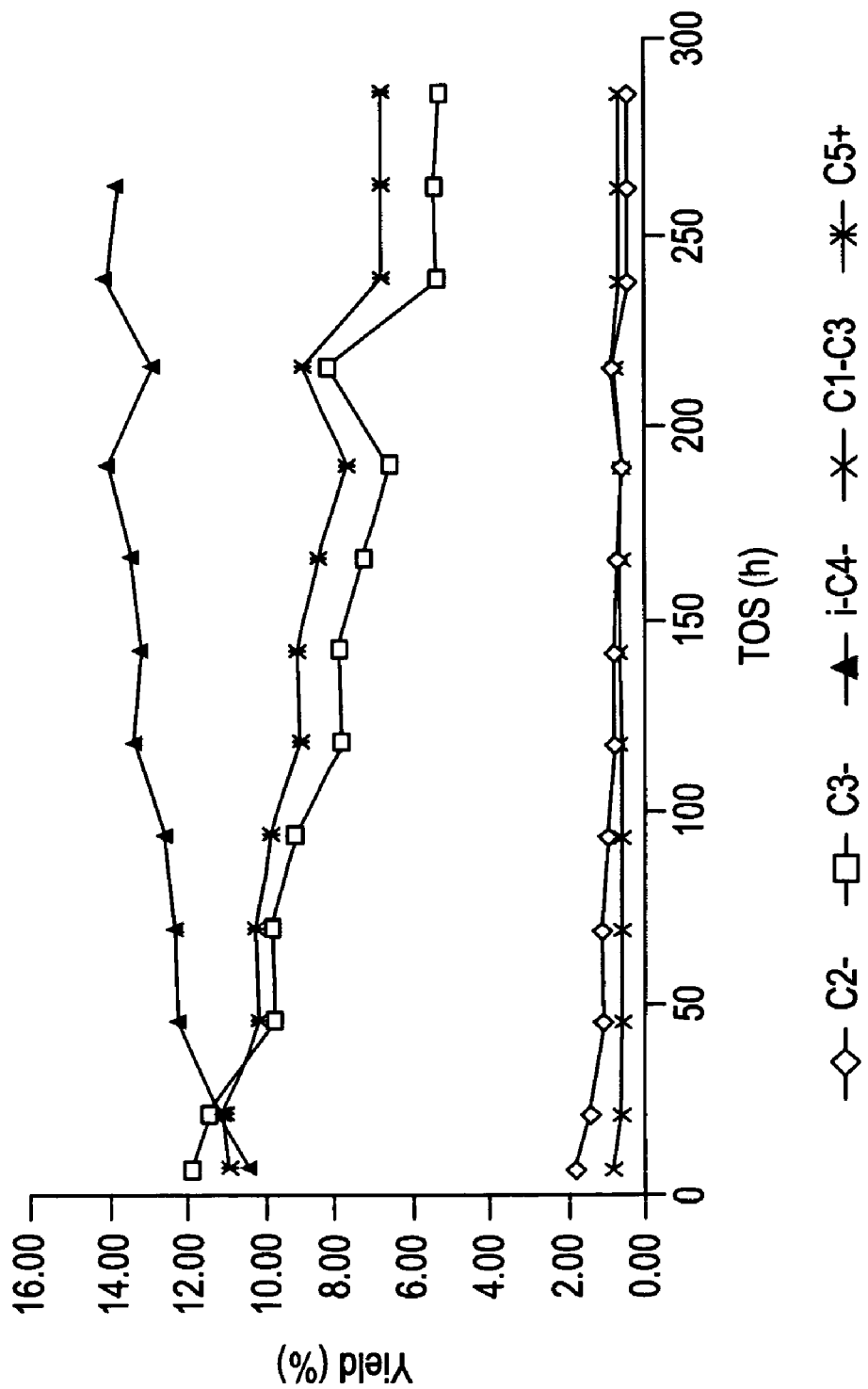

For Example 12, the same catalyst was employed but, in a manner similar to that for Example 7, the steaming and aluminum extraction steps were carried out prior to the extrusion step in which the silicalite catalyst was formulated with the binder comprising 50 wt % silica in the composite catalyst. It may be seen from FIG. 4 that for Example 12, the propylene yield decreased more significantly over time than for Example 11. This illustrates that for an amount of the binder of around 50% in the formulated silicalite catalyst, preferably the extrusion step is performed prior to the steaming and extraction steps.

Figure 5:
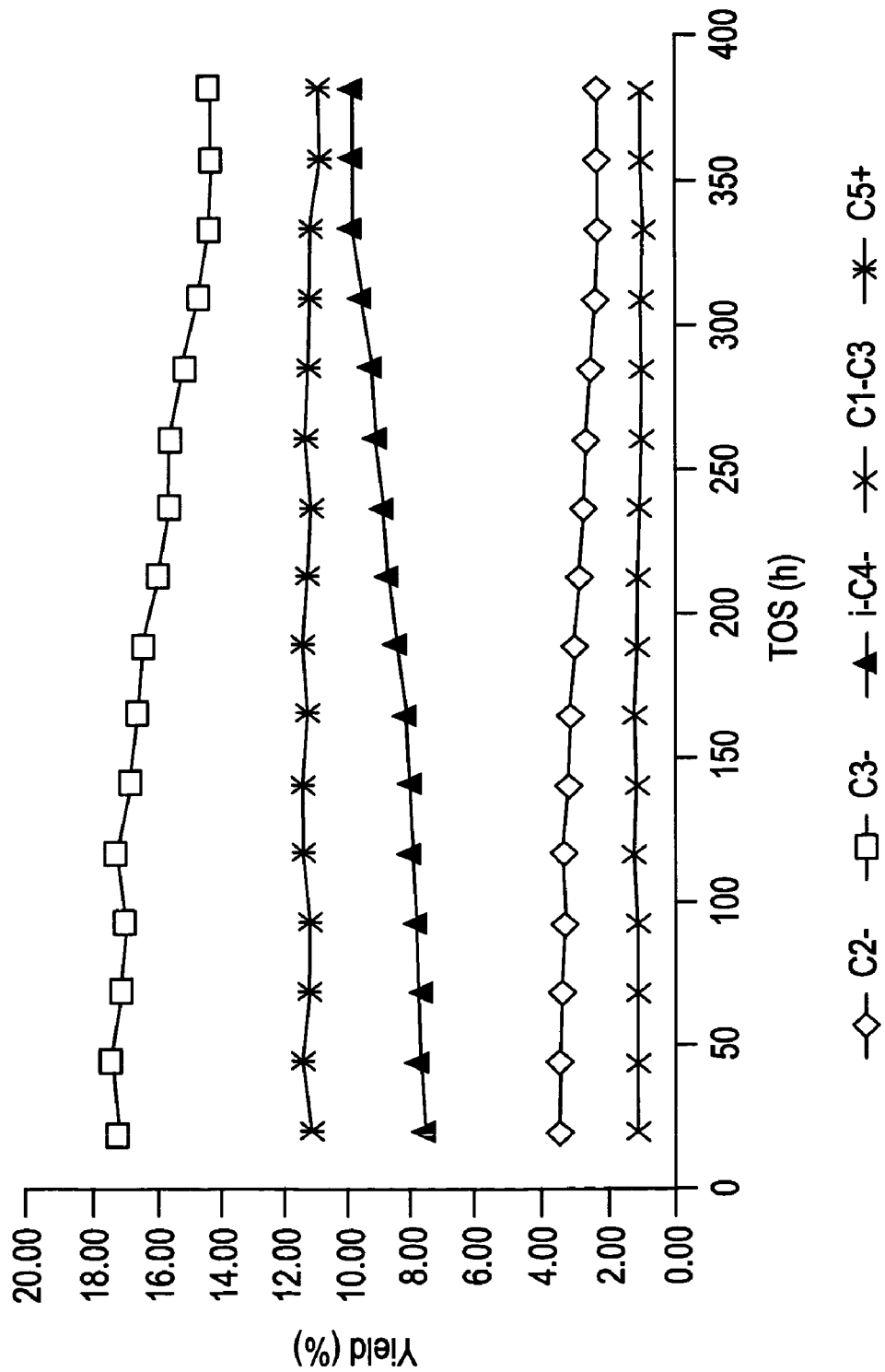

Example 13 was similar to Example 12 wherein the yield of propylene over time in a catalytic cracking process was studied using a catalyst similar to that of Example 11, but comprising only 20 wt % silica binder based on the weight of the formulated catalyst of silicalite with the binder. It may be seen from FIG. 5 that the yield of the propylene does not decrease as greatly over time as for Example 11 having a greater amount of binder in the catalyst. Thus this Example shows that for low binder amounts, the steaming and extraction steps can be carried out before the extrusion step wherein the catalyst is deposited on the binder, without significant decrease in the yield of propylene over time in the catalytic cracking process for olefinic feedstocks.

Figure 6:
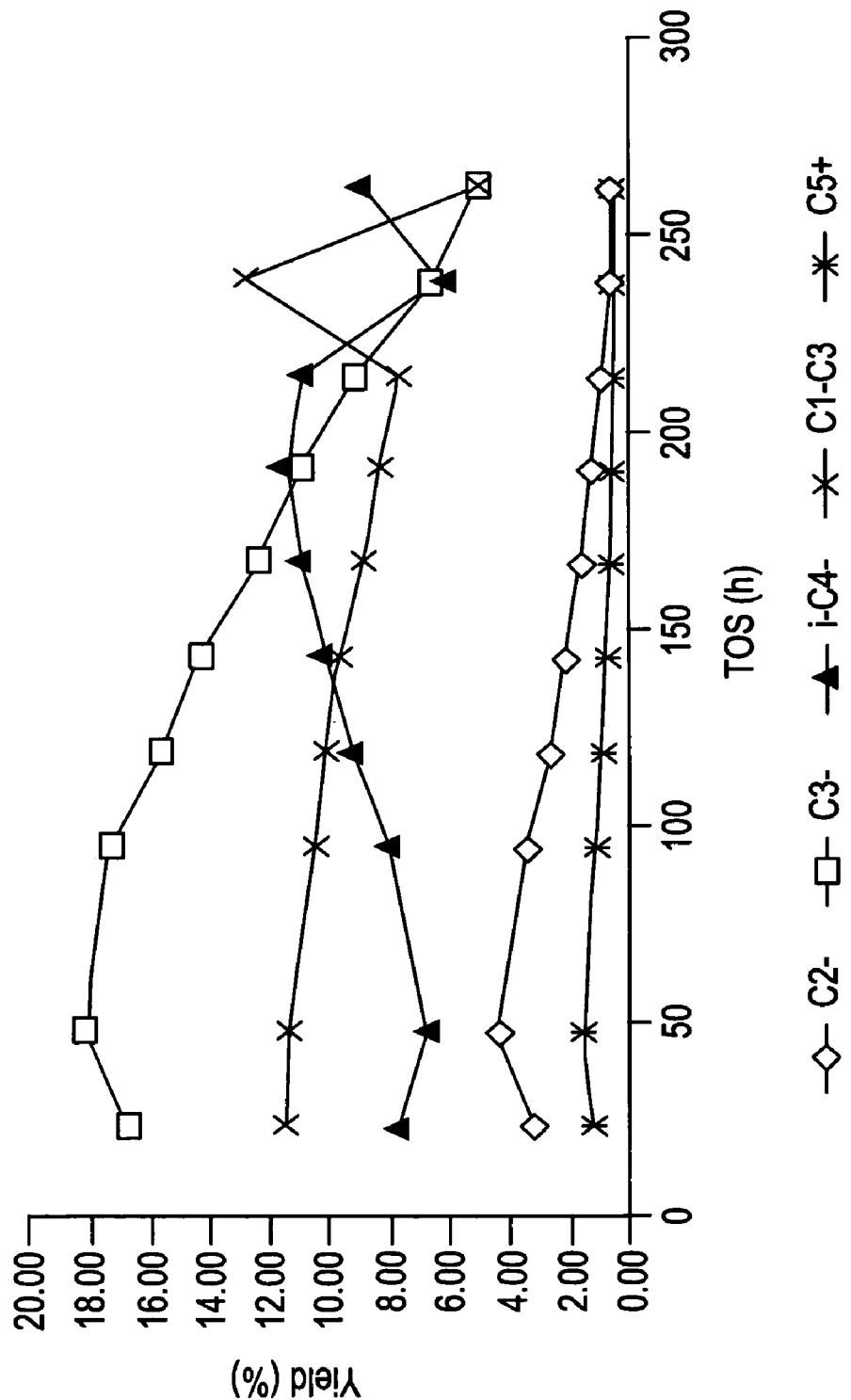

In Comparative Example 3 a silicalite catalyst was formed in a manner similar to that of Example 12 except that the binder comprised alumina rather than silica, with the alumina binder comprising 50 wt % of the silicalite/binder composite catalyst. The resultant catalyst was employed for the catalytic cracking of a $C_4$ (depleted in dienes) olefinic feedstock and the results are shown in FIG. 6. It may be seen that when an aluminum-containing binder, in particular alumina, is employed the yield of propylene from the catalytic cracking process is significantly decreased over time. It is believed that the high acidity of the aluminum-containing binder leads to coke formation on the catalyst which in turn leads to reduced activity of the catalyst over time in the catalytic cracking process for olefins.

EXAMPLE 14 AND COMPARATIVE EXAMPLE 4

Example 14 and Comparative Example 4 illustrate the preference for the use of diene removal of the feedstocks, in particular by the hydrogenation of the dienes in the feedstocks.

For Example 14, a silicalite (obtained from the company AKZO) having the following properties was employed: Si/Al atomic ratio of 111, surface area of 389 m$^2$/g, and a crystallite size of from 2 to 5 microns. The silicalite was pressed, crushed and the 35–45 mesh fraction retained. That fraction was treated at 553° C. with a steam atmosphere containing 72 vol % steam and 28 vol % nitrogen at atmospheric pressure for a period of around 48 hours. 104 g of the steamed catalyst was immersed in 1000 ml of an aqueous solution containing 0.025M of Na$_2$ EDTA and refluxed for a period of 16 hours. The slurry was washed thoroughly with water. Subsequently, the catalyst was exchanged with NH$_4$Cl (1000 ml of 0.05N per 100 g of catalyst) under reflux conditions. The catalyst was then finally washed, dried at 110° C. and calcined at 400° C. for 3 hours. The final Si/Al atomic ratio after the de-alumination process was 182.

Figure 7:
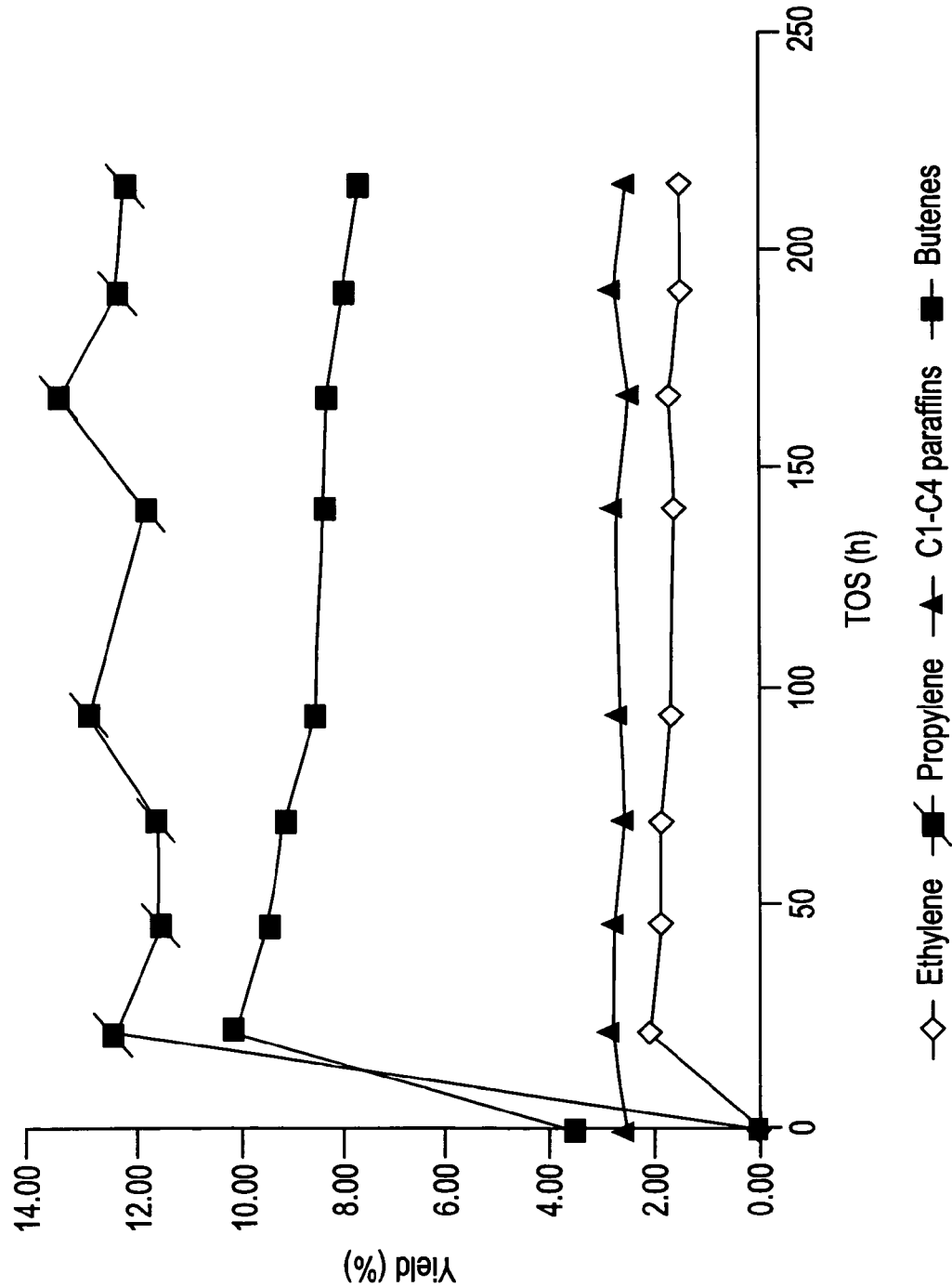
FIGS. 7 and 8 show the relationship between the yield of, inter alia, propylene with time for feedstocks which have and have not been subjected to a preliminary diene hydrogenation step prior to catalytic cracking.

The catalyst was then employed to crack a feed of light cracked naphtha containing 37 wt % olefins, the feed having being pre-treated in order to hydrogenate the dienes. The process conditions were an inlet temperature of 557° C., an outlet hydrocarbon pressure of atmospheric pressure and an LHSV of 25h$^{-1}$. FIG. 7 shows the distribution in the yield of ethylene, propylene, C$_1$ to C$_4$ paraffins and butenes over time. It may be seen from FIG. 7 that the production of propylene is stable over the tested time and there is no additional formation of paraffins.

In contrast, for Comparative Example 4 a silicalite catalyst was employed in an olefinic cracking process wherein the feed had not been prehydrotreated to hydrogenate the diene. The catalyst was the same catalyst produced in accordance with Example 4 having an Si/Al atomic ratio following de-alumination of 180. The catalyst was employed in a cracking process for a feed of LCN containing 49 wt % olefins, the feed including 0.5 wt % dienes. The process conditions were an outlet hydrocarbon pressure of atmospheric pressure, an inlet temperature of 570° C. and an LHSV of 27h$^{-1}$.

Figure 8:
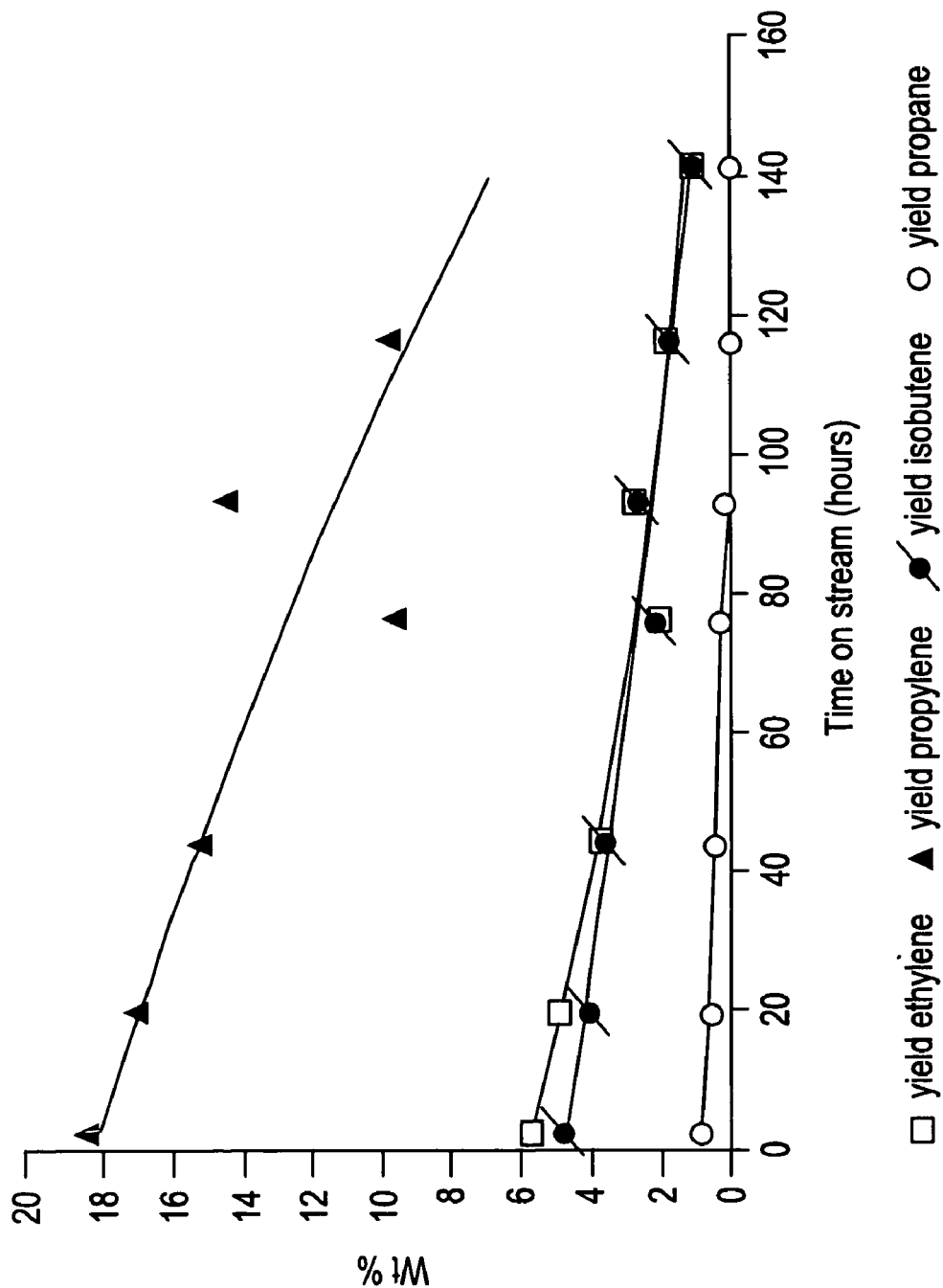
Figure 9:
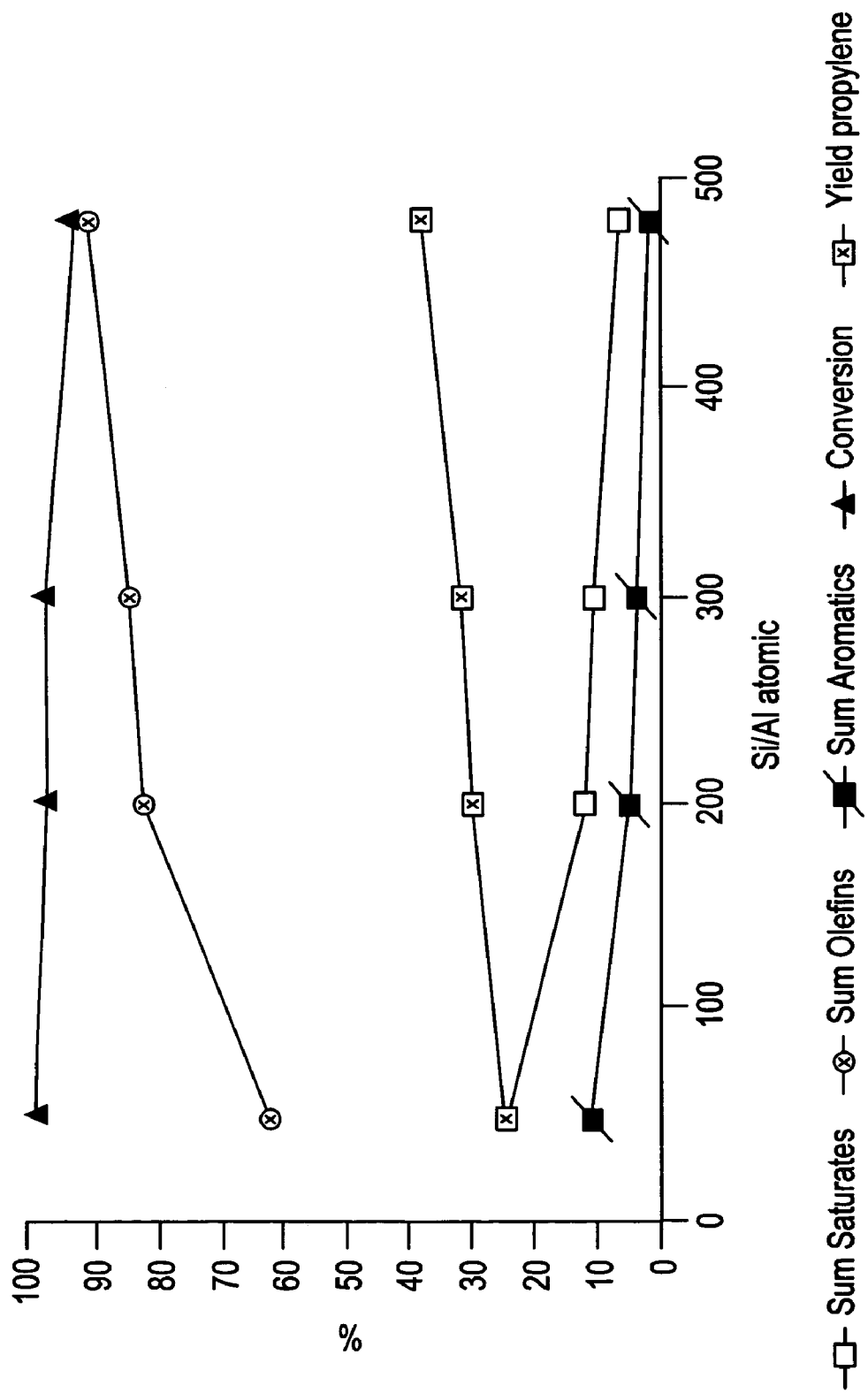
FIG. 9 shows the relationship between the amount of olefin feedstock conversion, the propylene yield, and the sum of the other components and the silicon/aluminum atomic ratio in a selective catalytic cracking process of the invention.

FIG. 8 shows the relationship between the yield of various olefinic components and propane with respect to time when the diene-containing low cracked naphtha is selectively cracked over the silicalite. It may be seen from Comparative Example 4 that the yield of propylene significantly decreases over time. It is believed that this results from the presence of dienes in the feedstock which can cause deposits of gum on the catalyst thereby reducing its activity over time.

EXAMPLE 15

In this Example, the feedstock comprised a first hydrocarbon stream comprising $C_4$ olefins, in particular a $C_4$ stream which had been subjected to diene hydrogenation and comprised $C_4$ olefins as the primary component thereof, and a second hydrocarbon stream comprising light cracked naphtha. The compositions of the two hydrocarbon streams and the resultant mixture are specified in Table 11. The mixed feedstock was fed over a silicalite catalyst at an inlet temperature for the feedstock of around 550° C., a hydrocarbon pressure of atmospheric pressure and an LHSV for the feedstock of around 23h$^{-1}$. It may be seen for this mixed feedstock, that the resultant effluent includes substantially the same olefin content as for the feedstock mixture and that the effluent includes 16.82% propylene. As described hereinabove, the use of a mixture of a $C_4$ olefin extreme and a LCN can lead to a decrease in the overall heat duty of the catalytic cracking process of the present invention.

EXAMPLE 16

In this Example, a feedstock comprising a 1-butene feed having the composition as specified in Table 14 was fed through a reactor at an inlet temperature of around 560° C., an outlet hydrocarbon pressure of atmospheric pressure and an LHSV of around 23h$^{-1}$ over a catalyst available in commerce from the company CU Chennie Ueticon AG of Switzerland under the trade mark ZEOCAT P2-2. The catalyst had a silicon/aluminium atomic ratio of 300. The catalyst was commercially available and had been prepared by crystallisation using an organic template and had been unsubjected to any subsequent steaming or de-alumination process. The crystal size of the catalyst was from 2 to 5 microns and the pellet size was from 35 to 45 mesh. The composition of the effluent was examined after 40 hours on stream and after 112 hours on stream and the results of the analysis of the effluent are indicated in Table 14. Table 14 shows that the catalyst having a silicon/aluminium atomic ratio of 300 has great stability with respect to the catalytic cracking process which is selective to propylene in the effluent. Thus after 40 hours on stream the propylene comprised 18.32 wt % in the effluent whereas after 112 hours on stream the propylene comprised 18.19 wt % of the effluent.

After 162 hours on stream the propylene comprised 17.89 wt % of the effluent. This shows that the propylene content in the effluent does not significantly reduce over quite significant periods of time of up to about 5 days, and more than 3 days. A period of 3 days is typically a recycling or regeneration period employed for two parallel "swing" reactors of the fixed bed type. The results of Example 16 after the periods of 112 hours and 162 hours may be respectively compared to those of Comparative Example 1 after the periods of 97 hours and 169 hours. For Comparative Example 1 the catalyst was reasonably stable over 97 hours, with a decrease in the propylene content in the effluent of around 1.1% as compared to the initial volume, but the stability decreased significantly between 97 hours and 169 hours, which is not the case for the corresponding periods of 112 hours and 162 hours for Example 16.

COMPARATIVE EXAMPLE 5

In this Comparative Example, a commercially available ZSM-5 catalyst having a silicon/aluminium atomic ratio of 25 was employed in the catalytic cracking of a feedstock comprising butene. In the catalytic cracking process, the butene-containing feedstock had the composition as specified in Table 15.

The catalytic cracking process was carried out at an inlet temperature of 560° C., an outlet hydrocarbon pressure of atmospheric pressure and an LHSV of 50h$^{-1}$.

The catalyst and the process conditions, in particular the high space velocity, were selected so as to simulate the corresponding catalyst and conditions disclosed in EP-A-0109059 referred to hereinabove.

The catalytic cracking process was performed for a period of nearly 40 hours and periodically the composition of the effluent was determined after successive periods of time on stream (TOS). The composition of the effluent, with a corresponding indication of the degree of conversion of the butenes, after particular times on stream are specified in Table 15.

It may be seen from Table 15 that when a ZSM-5 catalyst having a low silicon/aluminum atomic ratio of around 25 is employed in conjunction with high space velocities, which EP-A-0109059 indicates as being important for achieving high propylene yield, then although the propylene yield may be sufficiently high to yield around 16 wt % propylene in the effluent, this occurs after a period of around 15–20 hours on stream and after that period the propylene yield rapidly deteriorates. This indicates low catalyst stability with the use of a low silicon/aluminium atomic ratio in conjunction with a high space velocity as employed in the processes disclosed in EP-A-0109059.

TABLE 1

| COMPOSITION COMPOUND | | FEED LCN IN [wt %] | FEED hydrotreated IN [wt %] | After Cracking OUT [wt %] |
|---|---|---|---|---|
| $C_1$ | P1 | 0.0000 | 0.0000 | 0.2384 |
| $C_2$ | P2 | 0.0000 | 0.0000 | 0.3110 |
|  | O2 | 0.0000 | 0.0000 | 5.2737 |
| $C_3$ | P3 | 0.0000 | 0.0000 | 0.3598 |
|  | O3 | 0.0000 | 0.0000 | 18.3805 |
|  | D3 | 0.0000 | 0.0000 | 0.0030 |
| $C_4$ | iP4 | 0.2384 | 0.2182 | 0.5046 |
|  | nP4 | 0.5550 | 0.5509 | 0.8968 |
|  | iO4 | 0.0000 | 0.2932 | 4.56 |
|  | nO4 | 2.7585 | 3.0342 | 8.46 |
|  | D4 | 0.0073 | 0.0000 | 0.0000 |

TABLE 1-continued

| COMPOSITION | COMPOUND | FEED LCN IN [wt %] | FEED hydrotreated IN [wt %] | After Cracking OUT [wt %] |
|---|---|---|---|---|
| $C_5$ | iP5 | 16.5821 | 17.1431 | 18.2679 |
| | nP5 | 2.4354 | 2.5395 | 2.6388 |
| | cP5 | 0.4171 | 0.4239 | 0.7441 |
| | iO5 | 11.7637 | 12.1856 | 4.1256 |
| | nO5 | 9.6023 | 10.0095 | 2.1724 |
| | cO5 | 0.9141 | 0.9697 | 0.4796 |
| | D5 | 0.3803 | 0.0299 | 0.2446 |
| $C_6$ | iP6 | 14.5310 | 14.3130 | 13.4783 |
| | nP6 | 1.9391 | 1.8239 | 1.3217 |
| | cP6 | 3.5696 | 3.4544 | 2.6066 |
| | iO6 | 8.7439 | 8.5702 | 0.4966 |
| | nO6 | 6.6270 | 6.0716 | 1.4201 |
| | cO6 | 0.1956 | 0.1548 | 0.0748 |
| | D6 | 0.0000 | 0.0000 | 0.0000 |
| | A6 | 2.5282 | 2.8300 | 1.9257 |
| $C_7$ | iP7 | 5.6996 | 5.2747 | 4.3614 |
| | nP7 | 0.3809 | 0.3565 | 0.2911 |
| | cP7 | 2.3709 | 2.2277 | 1.6086 |
| | nO7 | 2.5260 | 2.3606 | 0.1396 |
| | iO7 | 0.6311 | 0.5455 | 0.0907 |
| | cO7 | 1.0705 | 1.0960 | 0.3972 |
| | D7 | 0.0000 | 0.0000 | 0.0000 |
| | A7 | 2.2029 | 2.0668 | 3.0112 |
| $C_8$ | iP8 | 1.0876 | 0.9917 | 0.9031 |
| | nP8 | 0.0000 | 0.0000 | 0.0000 |
| | cP8 | 0.2420 | 0.2217 | 0.1983 |
| | iO8 | 0.0000 | 0.0000 | 0.0000 |
| | nO8 | 0.0000 | 0.0000 | 0.0000 |
| | cO8 | 0.0000 | 0.0000 | 0.0000 |
| | A8 | 0.0000 | 0.2432 | 0.0000 |
| TOTAL | | 100.0000 | 100.0000 | 100.0000 |
| Paraffin | P1–P8 | 50.05 | 49.54 | 48.73 |
| Olefins | O2–O8 | 44.83 | 45.29 | 46.08 |
| Dienes | D3–D8 | 0.39 | 0.03 | 0.25 |
| Aromatics | A6–A8 | 4.73 | 5.14 | 4.94 |

TABLE 2

| COMPOSITION | COMPOUND | FEED LCN IN [wt %] | FEED hydrotreated IN [wt %] | After Cracking OUT [wt %] |
|---|---|---|---|---|
| $C_5$+ liquid product | | 96.4409 | 95.9035 | 60.9980 |
| COMPOSITION OF $C_5$+ | | | | |
| $C_5$ | iP5 | 17.1940 | 17.8753 | 29.9484 |
| | nP5 | 2.5253 | 2.6480 | 4.3260 |
| | cP5 | 0.4325 | 0.4420 | 1.2199 |
| | iO5 | 12.1978 | 12.7061 | 6.7635 |
| | nO5 | 9.9567 | 10.4370 | 3.5615 |
| | cO5 | 0.9479 | 1.0111 | 0.7862 |
| | D5 | 0.3943 | 0.0312 | 0.4010 |
| $C_6$ | iP6 | 15.0672 | 14.9244 | 22.0963 |
| | nP6 | 2.0106 | 1.9019 | 2.1668 |
| | cP6 | 3.7014 | 3.6019 | 4.2733 |
| | iO6 | 9.0666 | 8.9362 | 0.8141 |
| | nO6 | 6.8716 | 6.3310 | 2.3281 |
| | cO6 | 0.2028 | 0.1615 | 0.1226 |
| | D6 | 0.0000 | 0.0000 | 0.0000 |
| | A6 | 2.6215 | 2.9509 | 3.1569 |
| $C_7$ | iP7 | 5.9099 | 5.5000 | 7.1501 |
| | nP7 | 0.3949 | 0.3717 | 0.4773 |
| | cP7 | 2.4584 | 2.3229 | 2.6371 |
| | nO7 | 2.6193 | 2.4614 | 0.2289 |
| | iO7 | 0.6544 | 0.5689 | 0.1486 |
| | cO7 | 1.1100 | 1.1428 | 0.6511 |
| | D7 | 0.0000 | 0.0000 | 0.0000 |
| | A7 | 2.2842 | 2.1551 | 4.9365 |
| $C_8$ | iP8 | 1.1277 | 1.0340 | 1.4806 |
| | nP8 | 0.0000 | 0.0000 | 0.0000 |
| | cP8 | 0.2509 | 0.2312 | 0.3251 |
| | iO8 | 0.0000 | 0.0000 | 0.0000 |
| | nO8 | 0.0000 | 0.0000 | 0.0000 |

TABLE 2-continued

| COMPOSITION | COMPOUND | FEED LCN IN [wt %] | FEED hydrotreated IN [wt %] | After Cracking OUT [wt %] |
|---|---|---|---|---|
| | cO8 | 0.0000 | 0.0000 | 0.0000 |
| | A8 | 0.0000 | 0.2536 | 0.0000 |
| TOTAL | | 100.0000 | 100.0000 | 100.0000 |

TABLE 3

| COMPOSITION COMPOUND | FEED LCN IN [wt %] | FEED hydrotreated IN [wt %] | After Cracking OUT [wt %] |
|---|---|---|---|
| BREAK DOWN PER CARBON NUMBER | | | |
| $C_2$'s | | | |
| Ethane | | | 5.5683 |
| Ethylene | | | 94.4317 |
| $C_3$'s | | | |
| Propylene | | | 98.0643 |
| Propane | | | 1.9194 |
| Propadiene | | | 0.0162 |
| $C_4$'s | | | |
| iso-butane | 6.6982 | 5.3261 | 3.4953 |
| n-butane | 15.5935 | 13.4477 | 6.2125 |
| butenes | 77.5043 | 81.2262 | 90.2922 |
| butadiene | 0.2040 | 0.0000 | 0.0000 |

TABLE 4

| COMPOSITION | COMPOUND | FEED C5 cut LCN IN [wt %] | FEED hydro-treated IN [wt %] | After Cracking OUT [wt %] |
|---|---|---|---|---|
| $C_1$ | P1 | 0.0000 | 0.0000 | 0.2200 |
| $C_2$ | P2 | 0.0000 | 0.0023 | 0.3150 |
| | O2 | 0.0000 | 0.0701 | 6.7750 |
| $C_3$ | P3 | 0.0000 | 0.0509 | 0.3180 |
| | O3 | 0.0000 | 0.4950 | 16.7970 |
| | D3 | 0.0000 | 0.0000 | 0.0027 |
| $C_4$ | iP4 | 0.3920 | 0.3140 | 0.6245 |
| | nP4 | 1.0295 | 0.8188 | 1.2416 |
| | iO4 | 0.0000 | 0.2889 | 4.6400 |
| | nO4 | 5.6372 | 4.4752 | 8.6200 |
| | D4 | 0.0098 | 0.0028 | 0.0000 |
| $C_5$ | iP5 | 40.7065 | 40.4353 | 40.0408 |
| | nP5 | 5.4447 | 5.6559 | 5.4248 |
| | cP5 | 0.9484 | 0.8503 | 1.2787 |
| | iO5 | 21.9994 | 21.9264 | 5.6684 |
| | nO5 | 18.0459 | 18.4788 | 2.9835 |
| | cO5 | 1.5376 | 1.6388 | 0.5625 |
| | D5 | 0.5270 | 0.0434 | 0.2064 |
| $C_6$ | iP6 | 1.2635 | 1.6486 | 1.3138 |
| | nP6 | 0.0000 | 0.0305 | 0.0299 |
| | cP6 | 0.0000 | 0.0945 | 0.1634 |
| | iO6 | 1.1777 | 2.0074 | 0.4388 |
| | nO6 | 0.9080 | 0.2499 | 0.7593 |
| | cO6 | 0.0000 | 0.0033 | 0.0000 |
| | D6 | 0.0100 | 0.0000 | 0.0000 |
| | A6 | 0.0000 | 0.0561 | 0.5017 |
| $C_7$ | iP7 | 0.0000 | 0.1211 | 0.0879 |
| | nP7 | 0.0000 | 0.0080 | 0.0683 |
| | cP7 | 0.0000 | 0.0524 | 0.0422 |
| | nO7 | 0.0028 | 0.0561 | 0.1380 |
| | iO7 | 0.0000 | 0.0070 | 0.0282 |
| | cO7 | 0.0000 | 0.0235 | 0.1594 |
| | D7 | 0.0000 | 0.0000 | 0.0000 |
| | A7 | 0.0000 | 0.0514 | 0.4556 |
| $C_8$ | iP8 | 0.0000 | 0.0325 | 0.0647 |
| | nP8 | 0.0000 | 0.0000 | 0.0000 |
| | cP8 | 0.0000 | 0.0042 | 0.0144 |
| | iO8 | 0.0000 | 0.0000 | 0.0000 |

TABLE 4-continued

| COMPOSITION COMPOUND | | FEED C5 cut LCN IN [wt %] | FEED hydro-treated IN [wt %] | After Cracking OUT [wt %] |
|---|---|---|---|---|
| | nO8 | 0.0000 | 0.0000 | 0.0000 |
| | cO8 | 0.0000 | 0.0000 | 0.0000 |
| | A8 | 0.0000 | 0.0066 | 0.0000 |
| TOTAL | | 100.0000 | 100.0000 | 100.0000 |
| Paraffin | P1–P8 | 49.78 | 50.12 | 51.25 |
| Olefins | O2–O8 | 49.67 | 49.72 | 47.59 |
| Dienes | D3–D8 | 0.55 | 0.05 | 0.21 |
| Aromatics | A6–A8 | 0.00 | 0.11 | 0.96 |

TABLE 5

| COMPOSITION COMPOUND | | FEED C5 cut LCN IN [wt %] | FEED hydro-treated IN [wt %] | After Cracking OUT [wt %] |
|---|---|---|---|---|
| C5+ liquid product COMPOSITION OF C5+ | | 92.9315 | 93.4821 | 60.4308 |
| C5 | iP5 | 43.8026 | 43.2546 | 66.2589 |
| | nP5 | 5.8588 | 6.0502 | 8.9769 |
| | cP5 | 1.0206 | 0.9096 | 2.1160 |
| | iO5 | 23.6727 | 23.4552 | 9.3800 |
| | nO5 | 19.8059 | 19.7672 | 4.9371 |
| | cO5 | 1.6546 | 1.7531 | 0.9308 |
| | D5 | 0.5671 | 0.0465 | 0.3416 |
| C6 | iP6 | 1.3597 | 1.7636 | 2.1741 |
| | nP6 | 0.0000 | 0.0327 | 0.0495 |
| | cP6 | 0.0000 | 0.1011 | 0.2705 |
| | iO6 | 1.2673 | 2.1473 | 0.7262 |
| | nO6 | 0.9771 | 0.2673 | 1.2565 |
| | cO6 | 0.0000 | 0.0036 | 0.0000 |
| | D6 | 0.0107 | 0.0000 | 0.0000 |
| | A6 | 0.0000 | 0.0600 | 0.8302 |
| C7 | iP7 | 0.0000 | 0.1295 | 0.1454 |
| | nP7 | 0.0000 | 0.0085 | 0.1130 |
| | cP7 | 0.0000 | 0.0560 | 0.0698 |
| | nO7 | 0.0030 | 0.0601 | 0.2283 |
| | iO7 | 0.0000 | 0.0075 | 0.0467 |
| | cO7 | 0.0000 | 0.0252 | 0.2638 |
| | D7 | 0.0000 | 0.0000 | 0.0000 |
| | A7 | 0.0000 | 0.0550 | 0.7539 |
| C8 | iP8 | 0.0000 | 0.0348 | 0.1071 |
| | nP8 | 0.0000 | 0.0000 | 0.0000 |
| | cP8 | 0.0000 | 0.0044 | 0.0239 |
| | iO8 | 0.0000 | 0.0000 | 0.0000 |
| | nO8 | 0.0000 | 0.0000 | 0.0000 |
| | cO8 | 0.0000 | 0.0000 | 0.0000 |
| | A8 | 0.0000 | 0.0071 | 0.0000 |
| TOTAL | | 100.0000 | 100.0000 | 100.0000 |

TABLE 6

| COMPOSITION COMPOUND | FEED C5 cut LCN IN [wt %] | FEED hydrotreated IN [wt %] | After Cracking OUT [wt %] |
|---|---|---|---|
| BREAK DOWN PER CARBON NUMBER | | | |
| C2's | | | |
| Ethane | | | 4.4429 |
| Ethylene | | | 95.5571 |
| C3's | | | |
| Propylene | | | 98.1266 |
| Propane | | | 1.8575 |
| Propadiene | | | 0.0160 |
| C4's | | | |
| iso-butane | 5.5455 | 5.3219 | 4.1244 |
| n-butane | 14.5642 | 13.8795 | 8.2001 |
| butenes | 79.7517 | 80.7518 | 87.6755 |
| butadiene | 0.1385 | 0.0468 | 0.0000 |

TABLE 7

| COMPOSITION COMPOUND | | FEED C4 ex-MTBE IN [wt %] | FEED hydro-treated IN [wt %] | After Cracking OUT [wt %] |
|---|---|---|---|---|
| C1 | P1 | 0.0000 | 0.0000 | 0.1603 |
| C2 | P2 | 0.0000 | 0.0000 | 0.1326 |
| | O2 | 0.0000 | 0.0000 | 2.8470 |
| C3 | P3 | 0.2197 | 0.2676 | 0.4435 |
| | O3 | 0.0948 | 0.0969 | 15.1889 |
| | D3 | 0.0000 | 0.0000 | 0.0033 |
| C4 | iP4 | 33.9227 | 35.7281 | 35.7701 |
| | nP4 | 10.9638 | 11.6048 | 12.1288 |
| | iO4 | 0.0000 | 0.0000 | 8.5300 |
| | nO4 | 54.2396 | 52.0149 | 15.8000 |
| | D4 | 0.1861 | 0.0000 | 0.0000 |
| C5 | iP5 | 0.1433 | 0.1459 | 0.2292 |
| | nP5 | 0.0000 | 0.0000 | 0.0557 |
| | cP5 | 0.0000 | 0.0000 | 0.2266 |
| | iO5 | 0.2271 | 0.1342 | 3.8673 |
| | nO5 | 0.0030 | 0.0039 | 2.0472 |
| | cO5 | 0.0000 | 0.0000 | 0.1716 |
| | D5 | 0.0000 | 0.0000 | 0.1625 |
| C6 | iP6 | 0.0000 | 0.0010 | 0.0000 |
| | nP6 | 0.0000 | 0.0000 | 0.0135 |
| | cP6 | 0.0000 | 0.0000 | 0.0668 |
| | iO6 | 0.0000 | 0.0000 | 0.2930 |
| | nO6 | 0.0000 | 0.0000 | 0.5241 |
| | cO6 | 0.0000 | 0.0000 | 0.0514 |
| | D6 | 0.0000 | 0.0000 | 0.0000 |
| | A6 | 0.0000 | 0.0000 | 0.4443 |
| C7 | iP7 | 0.0000 | 0.0000 | 0.0240 |
| | nP7 | 0.0000 | 0.0000 | 0.0000 |
| | cP7 | 0.0000 | 0.0000 | 0.0590 |
| | nO7 | 0.0000 | 0.0000 | 0.1388 |
| | iO7 | 0.0000 | 0.0000 | 0.0661 |
| | cO7 | 0.0000 | 0.0000 | 0.1594 |
| | D7 | 0.0000 | 0.0000 | 0.0000 |
| | A7 | 0.0000 | 0.0006 | 0.2915 |
| C8 | iP8 | 0.0000 | 0.0000 | 0.0480 |
| | nP8 | 0.0000 | 0.0000 | 0.0000 |
| | cP8 | 0.0000 | 0.0000 | 0.0110 |
| | iO8 | 0.0000 | 0.0000 | 0.0000 |
| | nO8 | 0.0000 | 0.0000 | 0.0000 |
| | cO8 | 0.0000 | 0.0000 | 0.0000 |
| | A8 | 0.0000 | 0.0021 | 0.0000 |
| TOTAL | | 100.0000 | 100.0000 | 100.0000 |
| Paraffin | P1–P8 | 42.25 | 47.75 | 49.37 |
| Olefins | O2–O8 | 54.56 | 52.25 | 49.73 |
| Dienes | D3–D8 | 0.19 | 0.00 | 0.17 |
| Aromatics | A6–A8 | 0.00 | 0.00 | 0.74 |

TABLE 8

| COMPOSITION COMPOUND | | FEED C4 ex-MTBE IN [wt %] | FEED hydro-treated IN [wt %] | After Cracking OUT [wt %] |
|---|---|---|---|---|
| C5+ liquid product COMPOSITION OF C5+ | | 0.3733 | 0.2876 | 8.9513 |
| C5 | iP5 | 38.3749 | 50.7180 | 2.5610 |
| | nP5 | 0.0000 | 0.0000 | 0.6222 |
| | cP5 | 0.0000 | 0.0000 | 2.5317 |
| | iO5 | 60.8206 | 46.6722 | 43.2043 |
| | nO5 | 0.8045 | 1.3418 | 22.8709 |

TABLE 8-continued

| COMPOSITION COMPOUND | | FEED C₄ ex-MTBE IN [wt %] | FEED hydro-treated IN [wt %] | After Cracking OUT [wt %] |
|---|---|---|---|---|
| | cO5 | 0.0000 | 0.0000 | 1.9174 |
| | D5 | 0.0000 | 0.0000 | 1.8154 |
| C₆ | iP6 | 0.0000 | 0.3469 | 0.0000 |
| | nP6 | 0.0000 | 0.0000 | 0.1509 |
| | cP6 | 0.0000 | 0.0000 | 0.7467 |
| | iO6 | 0.0000 | 0.0000 | 3.2734 |
| | nO6 | 0.0000 | 0.0000 | 5.8548 |
| | cO6 | 0.0000 | 0.0000 | 0.5748 |
| | D6 | 0.0000 | 0.0000 | 0.0000 |
| | A6 | 0.0000 | 0.0000 | 4.9631 |
| C₇ | iP7 | 0.0000 | 0.0000 | 0.2681 |
| | nP7 | 0.0000 | 0.0000 | 0.0000 |
| | cP7 | 0.0000 | 0.0000 | 0.6589 |
| | nO7 | 0.0000 | 0.0000 | 1.5501 |
| | iO7 | 0.0000 | 0.0000 | 0.7386 |
| | cO7 | 0.0000 | 0.0000 | 1.7804 |
| | D7 | 0.0000 | 0.0000 | 0.0000 |
| | A7 | 0.0000 | 0.1991 | 3.2571 |
| C₈ | iP8 | 0.0000 | 0.0000 | 0.5368 |
| | nP8 | 0.0000 | 0.0000 | 0.0000 |
| | cP8 | 0.0000 | 0.0000 | 0.1233 |
| | iO8 | 0.0000 | 0.0000 | 0.0000 |
| | nO8 | 0.0000 | 0.0000 | 0.0000 |
| | cO8 | 0.0000 | 0.0000 | 0.0000 |
| | A8 | 0.0000 | 0.7220 | 0.0000 |
| TOTAL | | 100.00 | 100.00 | 100.00 |

TABLE 9

| COMPOSITION COMPOUND | FEED C₄ ex-MTBE IN [wt %] | FEED hydro-treated IN [wt %] | After Cracking OUT [wt %] |
|---|---|---|---|
| BREAK DOWN PER CARBON NUMBER | | | |
| C₂'s | | | |
| Ethane | | | 4.4489 |
| Ethylene | | | 95.5511 |
| C₃'s | | | |
| Propylene | 30.1496 | 26.5887 | 97.1426 |
| Propane | 69.8504 | 73.4113 | 2.8364 |
| Propadiene | 0.0000 | 0.0000 | 0.0209 |
| C₄'s | | | |
| iso-butane | 34.1577 | 35.9626 | 49.4929 |
| n-butane | 11.0397 | 11.6810 | 16.7819 |
| butenes | 54.6152 | 52.3564 | 33.7252 |
| butadiene | 0.1874 | 0.0000 | 0.0000 |

TABLE 10

| | Run 1 | Run 2 | Run 3 | Run 4 | Run 5 |
|---|---|---|---|---|---|
| T in (° C.) | 507 | 521 | 550 | 558 | 580 |
| LSHV (h⁻¹) | 25 | 25 | 25 | 25 | 25 |
| C₁ | 0.05 | 0.07 | 0.23 | 0.12 | 0.43 |
| C₂ | 0.06 | 0.08 | 0.27 | 0.17 | 0.47 |
| C₂⁼ | 2.86 | 3.32 | 4.91 | 4.17 | 5.69 |
| C₃ | 0.6 | 0.59 | 0.79 | 0.44 | 0.65 |
| C₃⁼ | 28.13 | 31.96 | 40.49 | 42.21 | 46.8 |
| C₄ | 0.66 | 0.53 | 0.51 | 0.2 | 0.24 |
| C₄⁼ | 19.68 | 18.81 | 18.29 | 16.09 | 14.9 |
| C₅ | 0.19 | 0.14 | 0 | 0 | 0.14 |
| C₅⁼ | 11.94 | 9.85 | 8.39 | 7.87 | 5.62 |
| C₆ | 3.08 | 2.91 | 2.22 | 3.09 | 3.25 |
| C₆⁼ | 24.96 | 27.76 | 17.95 | 20.01 | 15.77 |
| C₆+ | 7.79 | 3.98 | 5.95 | 5.63 | 6.04 |

TABLE 10-continued

| | Run 1 | Run 2 | Run 3 | Run 4 | Run 5 |
|---|---|---|---|---|---|
| CONVERSION | 73.5 | 71.67 | 82.05 | 75.31 | 82.98 |
| YIELD | 28.13 | 31.96 | 40.49 | 42.21 | 46.8 |

TABLE 11

| | | Run 1 | | Run 2 | |
|---|---|---|---|---|---|
| T in (° C.) | | 545 | | 549 | |
| LHSV (h⁻¹) | | 30 | | 30 | |
| Pressure/bara | | 1.2 | | 3 | |
| | | Feed | Effluent | Effluent | |
| C₁ | P1 | 0 | 0.2 | 0.4 | |
| C₂ | P2 | 0 | 0.1 | 0.4 | |
| | O2 | 0 | 4.4 | 5.3 | |
| C₃ | P3 | 0.3 | 1.1 | 4.3 | |
| | O3 | 0.1 | 19.6 | 13.3 | |
| C₄ | iP4 | 32.6 | 32.3 | 29.9 | |
| | nP4 | 10.2 | 10.8 | 10.7 | |
| | iO4 | 2.6 | 7.3 | 4.3 | |
| | nO4 | 53.5 | 11.2 | 6.6 | |
| C₅ | iP5 + nP5 + cP5 | 0.1 | 0.6 | 1.5 | |
| | iO5 + nO5 + cO5 | 0.4 | 5.6 | 4.1 | |
| C₆ | C6+ | 0.3 | 6.9 | 19.4 | |
| Sum | | | 100 | 100 | 100 |
| Olefins | O2–O5 | | 56.6 | 48.1 | 33.6 |
| Paraffins | P1–P5 | | 43.2 | 45.1 | 47.2 |
| Others & Unknown | | | 0.3 | 6.9 | 19.4 |

TABLE 12a

Example 8
Silicalite steamed and extracted

| T in (° C.) | | 545 | | |
|---|---|---|---|---|
| LHSV (h⁻¹) | | 30 | | |
| TOS (h) | | | 20 | 164 |
| | | Feed | Effluent | Effluent |
| Conversion of n-butenes | | | 79.2 | 75.1 |
| C₁ | P1 | 0 | 0.2 | 0.1 |
| C₂ | P2 | 0 | 0.1 | 0.1 |
| | O2 | 0 | 4.4 | 3.6 |
| C₃ | P3 | 0.3 | 1.1 | 0.9 |
| | O3 | 0.1 | 19.6 | 19.6 |
| C₄ | iP4 | 32.6 | 32.3 | 32.7 |
| | nP4 | 10.2 | 10.8 | 10.5 |
| | iO4 | 2.6 | 7.3 | 9 |
| | nO4 | 53.5 | 11.2 | 13.4 |
| C₅ | iP5 + nP5 + cP5 | 0.1 | 0.6 | 0.4 |
| | iO5 + nO5 + cO5 | 0.4 | 5.6 | 5.8 |
| C₆ | C6+ | 0.3 | 6.9 | 4 |
| Olefins | O2–O5 | | 56.6 | 48.1 | 51.4 |
| Paraffins | P1–P5 | | 43.2 | 45.1 | 44.7 |
| Others & Unknown | | | 0.3 | 6.9 | 4 |

TABLE 12b

Comparative Example 1
Silicalite non-modified (Si/Al = 120)

| T in (° C.) | 549 | | |
|---|---|---|---|
| LHSV (h⁻¹) | 30 | | |
| TOS (h) | | 5 | 97 | 169 |

TABLE 12b-continued

|   |   | Feed | Effluent | Effluent | Effluent |
|---|---|---|---|---|---|
| Conversion of n-butenes (%) | | | 85.20 | 79.90 | 55.90 |
| $C_1$ | P1 | 0.00 | 0.41 | 0.21 | 0.10 |
| $C_2$ | P2 | 0.00 | 0.51 | 0.17 | 0.00 |
| | O2 | 0.00 | 8.64 | 4.97 | 0.90 |
| $C_3$ | P3 | 0.30 | 3.80 | 1.61 | 0.40 |
| | O3 | 0.10 | 20.36 | 19.25 | 8.48 |
| $C_4$ | iP4 | 31.10 | 31.57 | 29.92 | 30.71 |
| | nP4 | 12.80 | 13.27 | 13.03 | 13.06 |
| | iO4 | 3.70 | 5.14 | 6.70 | 13.46 |
| | nO4 | 51.00 | 7.76 | 9.96 | 22.43 |
| $C_5$ | iP5 + nP5 + cP5 | 0.00 | 0.93 | 1.19 | 0.50 |
| | iO5 + nO5 + cO5 | 0.20 | 4.11 | 6.69 | 6.98 |
| $C_6$ | C6+ | 0.80 | 3.50 | 6.30 | 2.99 |
| Total | | 100.00 | 100.00 | 100.00 | 100.00 |
| Olefins | $O_2$–$O_5$ | 55.00 | 46.01 | 47.57 | 52.24 |
| Paraffins | $P_1$–$P_5$ | 44.20 | 50.49 | 46.13 | 44.77 |
| Others & Unknown | | 0.80 | 3.50 | 6.30 | 2.99 |
| Total | | 100.00 | 100.00 | 100.00 | 100.00 |

TABLE 12c

Comparative Example 2
Silicalite steamed

| T in (° C.) | 549 | | |
|---|---|---|---|
| LHSV ($h^{-1}$) | 29.6 | | |
| TOS (h) | | 16 | 72 |

|   |   | Feed | Effluent | Effluent |
|---|---|---|---|---|
| Conversion of n-butenes | | | 73.10 | 70.10 |
| $C_1$ | P1 | 0.00 | 0.20 | 0.10 |
| $C_2$ | P2 | 0.00 | 0.10 | 0.00 |
| | O2 | 0.00 | 2.73 | 1.71 |
| $C_3$ | P3 | 0.10 | 0.40 | 0.30 |
| | O3 | 0.30 | 17.89 | 14.27 |
| $C_4$ | iP4 | 33.40 | 33.87 | 33.16 |
| | nP4 | 9.70 | 10.11 | 10.15 |
| | iO4 | 2.40 | 10.11 | 10.75 |
| | nO4 | 53.20 | 14.47 | 15.99 |
| $C_5$ | iP5 + nP5 + cP5 | 0.50 | 0.51 | 0.50 |
| | iO5 + nO5 + cO5 | 0.10 | 7.18 | 8.54 |
| $C_6$ | C6+ | 0.30 | 2.43 | 4.52 |
| Total | | 100.00 | 100.00 | 100.00 |
| Olefins | $O_2$–$O_5$ | 56.00 | 52.38 | 51.26 |
| Paraffins | $P_1$–$P_5$ | 43.70 | 45.19 | 44.22 |
| Others & Unknown | | 0.30 | 2.43 | 4.52 |
| Total | | 100.00 | 100.00 | 100.00 |

TABLE 13

| COMPOSITION COMPOUND | C4-ex-EHPN IN [wt %] | LCN IN [wt %] | MIX IN [wt %] | OUT [wt%] |
|---|---|---|---|---|
| Paraffin | 45.10 | 58.99 | 52.25 | 53.07 |
| Olefins | 54.86 | 37.03 | 45.44 | 43.02 |
| Dienes | 0.04 | 0.01 | 0.05 | 0.28 |
| Aromatics | 0.00 | 3.97 | 2.26 | 3.64 |
| Total | 100.00 | 100.00 | 100.00 | 100.00 |
| Summary OF TOTAL | | | | |
| $C_1$ | | | | |
| P1 | 0.01 | 0.00 | 0.00 | 0.26 |

TABLE 13-continued

| COMPOSITION COMPOUND | C4-ex-EHPN IN [wt %] | LCN IN [wt %] | MIX IN [wt %] | OUT [wt%] |
|---|---|---|---|---|
| $C_2$ | | | | |
| P2 | 0.00 | 0.00 | 0.00 | 0.36 |
| O2 | 0.00 | 0.00 | 0.00 | 4.56 |
| $C_3$ | | | | |
| P3 | 0.22 | 0.00 | 0.08 | 0.85 |
| O3 | 0.06 | 0.00 | 0.02 | 16.82 |
| D3 | 0.01 | 0.00 | 0.00 | 0.00 |
| $C_4$ | | | | |
| iP4 | 29.40 | 1.04 | 12.32 | 13.60 |
| nP4 | 15.41 | 1.07 | 7.26 | 7.47 |
| iO4 | 2.55 | 0.23 | 3.71 | 5.48 |
| nO4 | 52.15 | 3.99 | 22.90 | 8.56 |
| D4 | 0.03 | 0.01 | 0.05 | 0.12 |
| $C_5$ | | | | |
| iP5 | 0.07 | 24.31 | 14.01 | 13.88 |
| nP5 | 0.00 | 3.42 | 1.95 | 1.97 |
| cP5 | 0.00 | 0.51 | 0.29 | 0.56 |
| iO5 | 0.09 | 11.09 | 6.35 | 3.11 |
| nO5 | 0.00 | 9.00 | 5.11 | 1.61 |
| cO5 | 0.00 | 0.68 | 0.38 | 0.23 |
| D5 | 0.00 | 0.00 | 0.00 | 0.15 |
| $C_6$ | | | | |
| iP6 | 0.00 | 14.66 | 8.19 | 7.72 |
| nP6 | 0.00 | 1.56 | 0.87 | 0.69 |
| cP6 | 0.00 | 3.27 | 1.83 | 1.31 |
| iO6 | 0.00 | 5.50 | 3.10 | 0.65 |
| nO6 | 0.01 | 3.45 | 2.15 | 1.35 |
| cO6 | 0.00 | 0.10 | 0.07 | 0.07 |
| D6 | 0.00 | 0.00 | 0.00 | 0.00 |
| A6 | 0.00 | 1.91 | 1.07 | 1.01 |
| $C_7$ | | | | |
| iP7 | 0.00 | 5.40 | 3.17 | 2.75 |
| nP7 | 0.00 | 0.37 | 0.21 | 0.16 |
| cP7 | 0.00 | 2.26 | 1.30 | 0.91 |
| nO7 | 0.00 | 1.86 | 0.92 | 0.20 |
| iO7 | 0.00 | 0.47 | 0.31 | 0.09 |
| cO7 | 0.00 | 0.67 | 0.42 | 0.29 |
| D7 | 0.00 | 0.00 | 0.00 | 0.00 |
| A7 | 0.00 | 2.01 | 1.14 | 1.80 |
| $C_8$ | | | | |
| iP8 | 0.00 | 0.88 | 0.57 | 0.45 |
| nP8 | 0.00 | 0.00 | 0.00 | 0.00 |
| cP8 | 0.00 | 0.24 | 0.21 | 0.12 |
| iO8 | 0.00 | 0.00 | 0.00 | 0.00 |
| nO8 | 0.00 | 0.00 | 0.00 | 0.00 |
| cO8 | 0.00 | 0.00 | 0.00 | 0.00 |
| A8 | 0.00 | 0.04 | 0.05 | 0.83 |
| | 100.00 | 100.00 | 100.00 | 100.00 |
| $C_5$ + liquid. OF $C_5$+ | 0.17 | 93.66 | 53.67 | 41.90 |
| $C_5$ | | | | |
| iP5 | 39.23 | 25.96 | 26.10 | 33.13 |
| nP5 | 0.00 | 3.65 | 3.63 | 4.71 |
| cP5 | 0.00 | 0.55 | 0.54 | 1.33 |
| iO5 | 53.28 | 11.84 | 11.84 | 7.43 |
| nO5 | 0.00 | 9.61 | 9.52 | 3.85 |
| cO5 | 0.00 | 0.72 | 0.71 | 0.56 |
| D5 | 0.00 | 0.00 | 0.00 | 0.36 |
| $C_6$ | | | | |
| iP6 | 0.00 | 15.65 | 15.26 | 18.43 |
| nP6 | 0.00 | 1.66 | 1.62 | 1.64 |
| cP6 | 0.00 | 3.49 | 3.41 | 3.12 |
| iO6 | 0.00 | 5.87 | 5.78 | 1.55 |
| nO6 | 7.49 | 3.69 | 4.00 | 3.22 |
| cO6 | 0.00 | 0.11 | 0.13 | 0.16 |

TABLE 13-continued

| COMPOSITION COMPOUND | C4-ex-EHPN IN [wt %] | LCN IN [wt %] | MIX IN [wt %] | OUT [wt%] |
|---|---|---|---|---|
| D6 | 0.00 | 0.00 | 0.00 | 0.00 |
| A6 | 0.00 | 2.04 | 2.00 | 2.41 |
| $C_7$ | | | | |
| iP7 | 0.00 | 5.76 | 5.91 | 6.56 |
| nP7 | 0.00 | 0.40 | 0.39 | 0.39 |
| cP7 | 0.00 | 2.41 | 2.43 | 2.17 |
| nO7 | 0.00 | 1.99 | 1.72 | 0.47 |
| iO7 | 0.00 | 0.50 | 0.58 | 0.21 |
| cO7 | 0.00 | 0.72 | 0.78 | 0.69 |
| D7 | 0.00 | 0.00 | 0.00 | 0.00 |
| A7 | 0.00 | 2.15 | 2.12 | 4.28 |
| $C_8$ | | | | |
| iP8 | 0.00 | 0.94 | 1.07 | 1.08 |
| nP8 | 0.00 | 0.00 | 0.00 | 0.00 |
| cP8 | 0.00 | 0.26 | 0.38 | 0.28 |
| iO8 | 0.00 | 0.00 | 0.00 | 0.00 |
| nO8 | 0.00 | 0.00 | 0.00 | 0.00 |
| cO8 | 0.00 | 0.00 | 0.00 | 0.00 |
| A8 | 0.00 | 0.05 | 0.10 | 1.98 |

TABLE 14

Example 16

Silicalite (Si/Al = 300)
T In (° C.) 560
LHSV ($h^{-1}$) 23

| TOS (h) | Feed | 40 Effluent | 112 Effluent | 162 Effluent |
|---|---|---|---|---|
| Conversion of n-butenes (%) | | 82.01 | 79.94 | 77.54 |
| $C_1$ | | | | |
| P1 | 0.01 | 0.31 | 0.25 | 0.20 |
| $C_2$ | | | | |
| P2 | 0.00 | 0.41 | 0.33 | 0.27 |
| O2 | 0.00 | 5.51 | 4.81 | 4.14 |
| $C_3$ | | | | |
| P3 | 0.22 | 2.02 | 1.54 | 1.23 |
| O3 | 0.06 | 18.32 | 18.19 | 17.89 |
| D3 | 0.01 | 0.00 | 0.00 | 0.00 |
| $C_4$ | | | | |
| iP4 | 29.40 | 29.26 | 28.45 | 28.15 |
| nP4 | 15.41 | 15.76 | 16.40 | 16.35 |
| iO4 | 2.55 | 6.03 | 6.80 | 7.51 |
| nO4 | 52.15 | 9.38 | 10.46 | 11.72 |
| D4 | 0.03 | 0.09 | 0.09 | 0.10 |
| $C_5$ | | | | |
| iP5 | 0.07 | 0.40 | 0.34 | 0.31 |
| nP5 | 0.00 | 0.21 | 0.18 | 0.15 |
| cP5 | 0.00 | 0.41 | 0.35 | 0.30 |
| iO5 | 0.09 | 3.31 | 3.65 | 4.01 |
| nO5 | 0.00 | 1.73 | 1.89 | 2.06 |
| cO5 | 0.00 | 0.20 | 0.20 | 0.20 |
| D5 | 0.00 | 0.14 | 0.14 | 0.13 |
| $C_6$ | | | | |
| iP6 | 0.00 | 0.04 | 0.03 | 0.02 |
| nP6 | 0.00 | 0.06 | 0.05 | 0.05 |
| cP6 | 0.00 | 0.43 | 0.34 | 0.27 |
| iO6 | 0.00 | 0.73 | 0.73 | 0.72 |
| nO6 | 0.01 | 1.50 | 1.37 | 1.24 |
| cO6 | 0.00 | 0.06 | 0.06 | 0.06 |
| D6 | 0.00 | 0.00 | 0.00 | 0.00 |
| A6 | 0.00 | 0.61 | 0.59 | 0.57 |
| $C_7$ | | | | |
| iP7 | 0.00 | 0.07 | 0.06 | 0.05 |
| nP7 | 0.00 | 0.00 | 0.00 | 0.00 |
| cP7 | 0.00 | 0.21 | 0.18 | 0.14 |
| iO7 | 0.00 | 0.17 | 0.20 | 0.19 |
| nO7 | 0.00 | 0.08 | 0.08 | 0.07 |
| cO7 | 0.00 | 0.33 | 0.23 | 0.19 |
| D7 | 0.00 | 0.00 | 0.00 | 0.00 |
| A7 | 0.00 | 1.06 | 0.94 | 0.77 |
| $C_8$ | | | | |
| iP8 | 0.00 | 0.09 | 0.09 | 0.09 |
| nP8 | 0.00 | 0.00 | 0.00 | 0.00 |
| cP8 | 0.00 | 0.03 | 0.01 | 0.01 |
| iO8 | 0.00 | 0.00 | 0.00 | 0.00 |
| nO8 | 0.00 | 0.00 | 0.00 | 0.00 |
| cO8 | 0.00 | 0.00 | 0.00 | 0.00 |
| A8 | 0.00 | 1.03 | 0.95 | 0.83 |
| Total | 100.00 | 100.00 | 100.00 | 100.00 |
| Paraffins (P) | 45.10 | 49.70 | 48.60 | 47.59 |
| Olefins (O) | 54.86 | 47.37 | 48.68 | 50.00 |
| Dienes (D) | 0.04 | 0.23 | 0.23 | 0.24 |
| Aromatics (A) | 0.00 | 2.70 | 2.49 | 2.17 |
| Total | 100.00 | 100.00 | 100.00 | 100.00 |

TABLE 15

Comparative Example 5
ZSM5 (Si/Al = 25)
T in (° C.) 560
LHSV(h-1) 50

| | Feed | 0.22 Effluent | 4.35 Effluent | 9.50 Effluent | 14.67 Effluent | 20.80 Effluent | 26.88 Effluent | 32.05 Effluent | 39.98 Effluent |
|---|---|---|---|---|---|---|---|---|---|
| Conversion of butenes | | 93.59 | 88.88 | 82.58 | 76.71 | 67.29 | 55.85 | 43.02 | 28.04 |
| $C_1$ P1 | 0.02 | 3.69 | 2.02 | 0.85 | 0.34 | 0.17 | 0.12 | 0.09 | 0.06 |

TABLE 15-continued

Comparative Example 5
ZSM5 (Si/Al = 25)
T in (° C.) 560
LHSV(h-1) 50

| | | | | | | | TOS (h) | | | |
|---|---|---|---|---|---|---|---|---|---|---|
| | | Feed | 0.22 Effluent | 4.35 Effluent | 9.50 Effluent | 14.67 Effluent | 20.80 Effluent | 26.88 Effluent | 32.05 Effluent | 39.98 Effluent |
| $C_2$ | P2 | 0.00 | 5.48 | 2.23 | 0.94 | 0.52 | 0.23 | 0.12 | 0.07 | 0.03 |
| | O2 | 0.00 | 4.29 | 6.26 | 6.92 | 5.32 | 3.36 | 1.88 | 1.07 | 0.37 |
| $C_3$ | P3 | 0.34 | 28.07 | 16.97 | 9.22 | 3.64 | 1.65 | 0.98 | 0.62 | 0.55 |
| | O3 | 0.12 | 6.05 | 9.36 | 12.81 | 15.99 | 16.04 | 13.09 | 10.03 | 5.48 |
| | D3 | 0.01 | 0.00 | 0.00 | 0.00 | 0.00 | 0.00 | 0.00 | 0.00 | 0.00 |
| $C_4$ | iP4 | 32.04 | 12.31 | 23.44 | 26.54 | 33.90 | 33.72 | 33.84 | 32.22 | 33.72 |
| | nP4 | 12.65 | 6.25 | 10.52 | 13.69 | 13.58 | 13.89 | 13.82 | 13.99 | 13.51 |
| | iO4 | 2.22 | 1.37 | 2.39 | 3.74 | 4.99 | 6.17 | 8.35 | 10.60 | 12.31 |
| | nO4 | 52.16 | 2.11 | 3.66 | 5.74 | 7.67 | 11.62 | 15.65 | 20.39 | 26.82 |
| | D4 | 0.05 | 0.03 | 0.06 | 0.09 | 0.11 | 0.10 | 0.04 | 0.05 | 0.06 |
| $C_5$ | iP5 | 0.25 | 0.87 | 1.10 | 1.11 | 0.59 | 0.44 | 0.34 | 0.34 | 0.23 |
| | nP5 | 0.00 | 0.39 | 0.56 | 0.54 | 0.31 | 0.18 | 0.10 | 0.06 | 0.02 |
| | cP5 | 0.00 | 0.12 | 0.24 | 0.39 | 0.31 | 0.19 | 0.10 | 0.05 | 0.01 |
| | iO5 | 0.12 | 0.62 | 1.17 | 2.08 | 2.89 | 4.19 | 4.87 | 4.81 | 3.29 |
| | nO5 | 0.01 | 0.32 | 0.61 | 1.09 | 1.50 | 2.17 | 2.53 | 2.51 | 1.73 |
| | cO5 | 0.00 | 0.05 | 0.07 | 0.11 | 0.13 | 0.15 | 0.12 | 0.09 | 0.05 |
| | D5 | 0.00 | 0.04 | 0.05 | 0.07 | 0.08 | 0.10 | 0.11 | 0.13 | 0.13 |
| $C_6$ | iP6 | 0.00 | 0.09 | 0.15 | 0.14 | 0.06 | 0.02 | 0.01 | 0.00 | 0.00 |
| | nP6 | 0.00 | 0.04 | 0.07 | 0.09 | 0.04 | 0.06 | 0.04 | 0.02 | 0.01 |
| | cP6 | 0.00 | 0.11 | 0.24 | 0.46 | 0.35 | 0.15 | 0.06 | 0.03 | 0.01 |
| | iO6 | 0.00 | 0.13 | 0.26 | 0.53 | 0.78 | 0.87 | 0.62 | 0.42 | 0.19 |
| | nO6 | 0.01 | 5.05 | 3.93 | 3.06 | 1.98 | 1.44 | 1.12 | 0.93 | 0.66 |
| | cO6 | 0.00 | 0.01 | 0.02 | 0.03 | 0.04 | 0.05 | 0.06 | 0.05 | 0.03 |
| | D6 | 0.00 | 0.00 | 0.00 | 0.00 | 0.00 | 0.00 | 0.00 | 0.00 | 0.00 |
| | A6 | 0.00 | 4.37 | 2.31 | 1.28 | 0.59 | 0.46 | 0.41 | 0.35 | 0.20 |
| $C_7$ | iP7 | 0.00 | 0.03 | 0.06 | 0.08 | 0.08 | 0.07 | 0.06 | 0.04 | 0.02 |
| | nP7 | 0.00 | 0.01 | 0.01 | 0.01 | 0.01 | 0.01 | 0.00 | 0.00 | 0.00 |
| | cP7 | 0.00 | 0.03 | 0.09 | 0.19 | 0.18 | 0.11 | 0.06 | 0.03 | 0.01 |
| | iO7 | 0.00 | 0.01 | 0.05 | 0.14 | 0.22 | 0.30 | 0.30 | 0.26 | 0.14 |
| | nO7 | 0.00 | 0.01 | 0.02 | 0.06 | 0.08 | 0.11 | 0.11 | 0.10 | 0.06 |
| | cO7 | 0.00 | 0.03 | 0.10 | 0.21 | 0.30 | 0.33 | 0.25 | 0.17 | 0.09 |
| | D7 | 0.00 | 0.00 | 0.00 | 0.00 | 0.00 | 0.00 | 0.00 | 0.00 | 0.00 |
| | A7 | 0.00 | 11.10 | 6.83 | 4.15 | 1.72 | 0.79 | 0.38 | 0.21 | 0.06 |
| $C_8$ | iP8 | 0.00 | 0.01 | 0.01 | 0.03 | 0.05 | 0.07 | 0.07 | 0.08 | 0.04 |
| | nP8 | 0.00 | 0.00 | 0.00 | 0.00 | 0.00 | 0.00 | 0.00 | 0.00 | 0.00 |
| | cP8 | 0.00 | 0.00 | 0.01 | 0.02 | 0.02 | 0.02 | 0.02 | 0.02 | 0.02 |
| | iO8 | 0.00 | 0.00 | 0.00 | 0.00 | 0.00 | 0.00 | 0.00 | 0.00 | 0.00 |
| | nO8 | 0.00 | 0.00 | 0.00 | 0.00 | 0.00 | 0.00 | 0.00 | 0.00 | 0.00 |
| | cO8 | 0.00 | 0.00 | 0.00 | 0.00 | 0.00 | 0.00 | 0.00 | 0.00 | 0.00 |
| | A8 | 0.00 | 6.88 | 5.12 | 3.58 | 1.63 | 0.77 | 0.38 | 0.21 | 0.07 |
| Total | | 100.00 | 100.00 | 100.00 | 100.00 | 100.00 | 100.00 | 100.00 | 100.00 | 100.00 |
| Paraffins | | 45.29 | 57.53 | 57.72 | 54.31 | 53.99 | 50.97 | 49.72 | 47.65 | 48.25 |
| Olefins | | 54.64 | 20.05 | 27.90 | 36.52 | 41.88 | 46.81 | 48.95 | 51.41 | 51.23 |
| Dienes | | 0.07 | 0.07 | 0.11 | 0.16 | 0.19 | 0.20 | 0.15 | 0.17 | 0.19 |
| Aromatics | | 0.00 | 22.35 | 14.26 | 9.01 | 3.94 | 2.02 | 1.17 | 0.76 | 0.33 |
| Total | | 100.00 | 100.00 | 100.00 | 100.00 | 100.00 | 100.00 | 100.00 | 100.00 | 100.00 |

Paraffins = P
Olefins = O
Dienes = D
Aromatics = A

What is claimed is:

1. A process for the production of propylene from an olefinic feedstock containing at least one olefin of $C_4$ or greater comprising:
 (a) providing a crystalline silicate catalyst having an MFI structure and containing aluminum and silicon in the catalyst framework to provide a silicon/aluminum atomic ratio;
 (b) subjecting said catalyst to a pretreatment procedure involving heating the catalyst in steam and thereafter de-aluminating the catalyst by treating the catalyst with a complexing agent for aluminum to remove aluminum from the catalyst framework and providing a catalyst of increased silicon/aluminum atomic ratio within the range of 180 to 1000; and
 (c) contacting the pretreated catalyst with the olefinic feedstock containing at least one olefin of $C_4$ or greater to produce an effluent containing propylene in which the propylene yield on an olefin basis is from 30 to 50% based on the olefinic content of the feedstock.

2. A process according to claim 1, wherein at least 95 wt. % of any $C_3$ compounds in the effluent are present as propylene.

3. A process according to claim 1, wherein the feedstock contacts the catalyst at an inlet temperature of from 500 to 600° C.

4. A process according to claim 1, wherein the feedstock is passed over the catalyst at an LHSV of from 10 to $30h^{-1}$.

5. A process according to claim 1, wherein the catalyst of the MFI structure is silicalite.

6. A process according to claim 1, wherein the catalyst of the MFI structure is ZSM-5.

7. A process for the production of propylene from an olefinic feedstock containing at least one olefin of $C_4$ or greater comprising:
   (a) providing a crystalline silicate catalyst having an MFI structure and containing aluminum and silicon in the catalyst framework to provide a silicon/aluminum atomic ratio;
   (b) subjecting said catalyst to a pretreatment procedure involving heating the catalyst in steam to reduce tetrahedral aluminum in the catalyst framework and form amorphous alumina in the pores of the catalyst;
   (c) thereafter de-aluminating the catalyst by treating the catalyst with a complexing agent for aluminum to remove amorphous alumina from the catalyst framework and provide a catalyst of increased silicon/aluminum atomic ratio within the range of 180 to 1000; and
   (d) contacting the pretreated catalyst with the olefinic feedstock containing at least one olefin of $C_4$ or greater to produce an effluent containing propylene in which the propylene yield on an olefin basis is from 30 to 50 wt. % based on the olefinic content of the feedstock.

8. The process of claim 7 wherein said catalyst is silicalite and is heated in steam to a temperature within the range of 425°–870° C.

* * * * *